US012747289B2

(12) United States Patent
Barnthouse et al.

(10) Patent No.: US 12,747,289 B2
(45) Date of Patent: Sep. 29, 2026

(54) MANUFACTURING METHODS FOR PRODUCING ANTI-IL12/IL23 ANTIBODY COMPOSITIONS

(71) Applicant: Janssen Biotech, Inc., Horsham, PA (US)

(72) Inventors: Kristopher Barnthouse, Pottstown, PA (US); Subinay Ganguly, Newtown, PA (US); Maarten Groeneveld, Oegstgeest (NL); Manuel Lopez, Jr., Devon, PA (US); Michael Nedved, Downingtown, PA (US); Kevin D. Smith, Philadelphia, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 18/427,000

(22) Filed: Jan. 30, 2024

(65) Prior Publication Data

US 2024/0383976 A1 Nov. 21, 2024

Related U.S. Application Data

(63) Continuation of application No. 16/816,814, filed on Mar. 12, 2020, now abandoned.

(60) Provisional application No. 62/818,359, filed on Mar. 14, 2019.

(51) Int. Cl.
*C07K 16/24* (2006.01)
*C07K 1/18* (2006.01)
*C12N 5/071* (2010.01)

(52) U.S. Cl.
CPC .............. *C07K 16/244* (2013.01); *C07K 1/18* (2013.01); *C07K 2317/14* (2013.01); *C07K 2317/31* (2013.01); *C12N 5/0682* (2013.01)

(58) Field of Classification Search
None
See application file for complete search history.

(56) References Cited

U.S. PATENT DOCUMENTS 3,773,919 A 11/1973 Boswell
4,239,754 A 12/1980 Bertrand
4,309,989 A 1/1982 Fahim
4,399,216 A 8/1983 Axel
4,634,665 A 1/1987 Axel
4,656,134 A 4/1987 Ringold
4,668,218 A 5/1987 Virtanen
4,683,195 A 7/1987 Mullis
4,683,202 A 7/1987 Mullis
4,704,692 A 11/1987 Ladner
4,766,067 A 8/1988 Biswas
4,767,402 A 8/1988 Kost
4,795,699 A 1/1989 Tabor
4,800,159 A 1/1989 Mullis
4,816,567 A 3/1989 Cabilly
4,873,316 A 10/1989 Meade
4,889,818 A 12/1989 Gelfand
4,921,794 A 5/1990 Tabor
4,925,673 A 5/1990 Steiner
4,939,666 A 7/1990 Hardman
4,946,778 A 8/1990 Ladner
4,956,288 A 9/1990 Barsoum
4,965,188 A 10/1990 Mullis
4,994,370 A 2/1991 Silver
5,066,584 A 11/1991 Gyllensten
5,091,310 A 2/1992 Innis
5,116,964 A 5/1992 Capon
5,122,464 A 6/1992 Wilson
5,130,238 A 7/1992 Malek
5,142,033 A 8/1992 Innis
5,149,636 A 9/1992 Axel
5,168,062 A 12/1992 Stinski
5,179,017 A 1/1993 Axel
5,223,409 A 6/1993 Ladner
5,225,538 A 7/1993 Capon
5,225,539 A 7/1993 Winter
5,231,024 A 7/1993 Moeller
5,260,203 A 11/1993 Ladner
5,266,491 A 11/1993 Nagata
5,304,489 A 4/1994 Rosen
5,385,839 A 1/1995 Stinski
5,403,484 A 4/1995 Ladner
5,404,871 A 4/1995 Goodman
5,427,908 A 6/1995 Dower
5,447,851 A 9/1995 Beutler
5,455,030 A 10/1995 Ladner
5,457,038 A 10/1995 Trinchieri
5,458,135 A 10/1995 Patton
5,514,670 A 5/1996 Friedman
5,518,889 A 5/1996 Ladner (Continued)

FOREIGN PATENT DOCUMENTS

CL 6882000 3/2000
CN 101052726 A 10/2007

(Continued)

OTHER PUBLICATIONS

US 5,733,746 A, 03/1998, Treco (withdrawn)
Whitelam, et al., "Antibody production in transgenic plants," Biochemical Society Transactions, Transgenic Plants and Plan Biochemistry, vol. 22 (1994), pp. 940-944.
Yu, C., et al., "At least two Fc Neu5Gc residues of monoclonal antibodies are required for binding to anti-Neu5Gc antibody", Sci Rep., vol. 6 (2016), Article No. 20029, 11 pages.
Zhao Dongli, et al., IL-12 family asnd autimmune thyroid disease, 2014, Modern Medical Jounral vol. 45, No. 8, pp. 1171-1175.
A. U. Gubler et al (Clonic and Expression of Cytotoxic Lymphocyte Maturation Factor (CLMF) a Heterodimeric Lymphokine That Potentiates NR. LAK NA D T-Cell Reponses) Abstracts Journal of celluar Biochemistry Supplement 15 F: 70 (1991) 1 page.

(Continued)

*Primary Examiner* — Misook Yu
*Assistant Examiner* — Cheom-Gil Cheong
(74) *Attorney, Agent, or Firm* — Riverside Law LLP

(57) ABSTRACT

Methods of manufacture for producing anti-IL-12/IL-23p40 antibodies, e.g., the anti-IL-12/IL-23p40 antibody ustekinumab, in CHO and specific pharmaceutical compositions of the antibody are useful in treating various diseases.

4 Claims, 9 Drawing Sheets

Specification includes a Sequence Listing.

(56) References Cited

U.S. PATENT DOCUMENTS

| | | | |
|---|---|---|---|
| 5,530,101 | A | 6/1996 | Queen |
| 5,534,621 | A | 7/1996 | Ladner |
| 5,545,806 | A | 8/1996 | Lonberg |
| 5,545,807 | A | 8/1996 | Surani |
| 5,547,852 | A | 8/1996 | Seiler |
| 5,565,362 | A | 10/1996 | Rosen |
| 5,569,825 | A | 10/1996 | Lonberg |
| 5,571,698 | A | 11/1996 | Ladner |
| 5,576,195 | A | 11/1996 | Robinson |
| 5,580,717 | A | 12/1996 | Dower |
| 5,580,734 | A | 12/1996 | Treco |
| 5,585,089 | A | 12/1996 | Queen |
| 5,595,898 | A | 1/1997 | Robinson |
| 5,618,920 | A | 4/1997 | Robinson |
| 5,625,126 | A | 4/1997 | Lonberg |
| 5,625,825 | A | 4/1997 | Rostoker |
| 5,627,052 | A | 5/1997 | Schrader |
| 5,633,425 | A | 5/1997 | Lonberg |
| 5,641,670 | A | 6/1997 | Treco |
| 5,643,768 | A | 7/1997 | Kawasaki |
| 5,648,467 | A | 7/1997 | Trinchieri |
| 5,656,730 | A | 8/1997 | Lee |
| 5,658,754 | A | 8/1997 | Kawasaki |
| 5,661,016 | A | 8/1997 | Lonberg |
| 5,693,493 | A | 12/1997 | Robinson |
| 5,693,762 | A | 12/1997 | Queen |
| 5,698,417 | A | 12/1997 | Robinson |
| 5,698,435 | A | 12/1997 | Robinson |
| 5,714,352 | A | 2/1998 | Jakobovits |
| 5,723,323 | A | 3/1998 | Kauffman |
| 5,733,761 | A | 3/1998 | Treco |
| 5,750,373 | A | 5/1998 | Garrard |
| 5,763,192 | A | 6/1998 | Kauffman |
| 5,763,733 | A | 6/1998 | Whitlow |
| 5,766,886 | A | 6/1998 | Studnicka |
| 5,767,260 | A | 6/1998 | Whitlow |
| 5,770,198 | A | 6/1998 | Coller |
| 5,770,222 | A | 6/1998 | Unger |
| 5,770,359 | A | 6/1998 | Wilson |
| 5,770,428 | A | 6/1998 | Boris-Lawrie |
| 5,780,597 | A | 7/1998 | Gately |
| 5,789,650 | A | 8/1998 | Lonberg |
| 5,811,523 | A | 9/1998 | Trinchieri |
| 5,814,476 | A | 9/1998 | Kauffman |
| 5,814,599 | A | 9/1998 | Mitragotri |
| 5,817,483 | A | 10/1998 | Kauffman |
| 5,824,514 | A | 10/1998 | Kauffman |
| 5,827,690 | A | 10/1998 | Meade |
| 5,827,739 | A | 10/1998 | Wilson |
| 5,837,500 | A | 11/1998 | Ladner |
| 5,839,446 | A | 11/1998 | Waner |
| 5,849,695 | A | 12/1998 | Cohen |
| 5,849,992 | A | 12/1998 | Meade |
| 5,851,198 | A | 12/1998 | Castellano |
| 5,856,456 | A | 1/1999 | Whitlow |
| 5,871,753 | A | 2/1999 | Crabtree |
| 5,879,681 | A | 3/1999 | Leone-Bay |
| 5,885,793 | A | 3/1999 | Griffiths |
| 5,891,680 | A | 4/1999 | Lieschke |
| 5,976,862 | A | 11/1999 | Kauffman |
| 5,994,616 | A | 11/1999 | Rosen |
| 6,086,876 | A | 7/2000 | Karp |
| 6,171,825 | B1 | 1/2001 | Chan |
| 6,180,370 | B1 | 1/2001 | Queen |
| 6,204,023 | B1 | 3/2001 | Robinson |
| 6,225,117 | B1 | 5/2001 | Gately |
| 6,300,478 | B1 | 10/2001 | Trinchieri |
| 6,338,848 | B1 | 1/2002 | Leonard |
| 6,495,667 | B1 | 12/2002 | Bazan |
| 6,914,128 | B1 | 7/2005 | Salfeld |
| 6,936,441 | B2 | 8/2005 | Reiter |
| 7,250,165 | B2 | 7/2007 | Heavner |
| 8,975,040 | B2 | 3/2015 | Naso |
| 10,765,724 | B2 | 9/2020 | Chevrier |
| 10,844,416 | B2 | 11/2020 | Tescione |
| 11,014,982 | B2 | 5/2021 | Harrison |
| 11,041,020 | B2 | 6/2021 | Harrison |
| 11,197,913 | B2 | 12/2021 | Chevrier |
| 2003/0003097 | A1 | 1/2003 | Reff |
| 2003/0095976 | A1 | 5/2003 | Fitzpatrick |
| 2007/0212770 | A1 | 9/2007 | Grillberger |
| 2008/0009040 | A1 | 1/2008 | Grillberger |
| 2009/0182127 | A1 | 7/2009 | Kjaergaard |
| 2010/0015133 | A1 | 1/2010 | Igawa |
| 2010/0028637 | A1 | 2/2010 | Tavsanli |
| 2011/0123532 | A1 | 5/2011 | Gurney |
| 2012/0149876 | A1 | 6/2012 | Von Kreudenstein |
| 2013/0195849 | A1 | 8/2013 | Spreter Von Kreudenstein |
| 2019/0324000 | A1 | 10/2019 | Randolph |
| 2020/0291107 | A1 | 9/2020 | Barnthouse |
| 2023/0038355 | A1 | 2/2023 | Donlon |

FOREIGN PATENT DOCUMENTS

| | | | |
|---|---|---|---|
| CN | 105658799 | A | 6/2016 |
| CN | 109072303 | | 12/2018 |
| EP | 229246 | | 10/1986 |
| EP | 0218868 | A2 | 4/1987 |
| EP | 0288088 | | 10/1988 |
| EP | 368684 | | 5/1990 |
| EP | 371998 | | 6/1990 |
| EP | 0237507 | B1 | 12/1991 |
| EP | 550400 | | 7/1993 |
| EP | 0229246 | B1 | 8/1993 |
| EP | 0368684 | B1 | 3/1994 |
| EP | 0371998 | B1 | 3/1994 |
| EP | 0590689 | A2 | 4/1994 |
| EP | 0229046 | B1 | 5/1994 |
| EP | 0640689 | | 3/1995 |
| EP | 0438474 | B1 | 5/1996 |
| EP | 0710719 | A1 | 5/1996 |
| EP | 0463151 | B1 | 6/1996 |
| EP | 0550400 | B1 | 7/1996 |
| EP | 790255 | | 8/1997 |
| EP | 0814159 | A2 | 12/1997 |
| EP | 0814259 | | 12/1997 |
| EP | 433827 | | 3/1998 |
| EP | 804581 | | 9/2001 |
| EP | 0590689 | B1 | 5/2002 |
| EP | 1137766 | | 9/2005 |
| EP | 0710719 | B1 | 3/2007 |
| EP | 3059309 | | 8/2016 |
| EP | 3059319 | A1 | 8/2016 |
| EP | 3110961 | | 1/2017 |
| EP | 3323826 | A1 | 5/2018 |
| GB | 2272400 | A | 5/1994 |
| GB | 2272440 | A | 5/1994 |
| JP | 2016533769 | | 11/2016 |
| WO | 8605803 | A1 | 10/1986 |
| WO | 8806630 | A1 | 9/1988 |
| WO | 8906283 | A1 | 7/1989 |
| WO | 9003809 | A1 | 4/1990 |
| WO | 9004036 | A1 | 4/1990 |
| WO | 9005147 | | 5/1990 |
| WO | 1990005370 | | 5/1990 |
| WO | 9014424 | A1 | 11/1990 |
| WO | 9014430 | A1 | 11/1990 |
| WO | 9014443 | A1 | 11/1990 |
| WO | 9102078 | A1 | 2/1991 |
| WO | 9117271 | A1 | 11/1991 |
| WO | 9118980 | A1 | 12/1991 |
| WO | 9119818 | A1 | 12/1991 |
| WO | 1992001047 | A1 | 1/1992 |
| WO | 1992003461 | | 3/1992 |
| WO | 9205256 | | 4/1992 |
| WO | 9205258 | A1 | 4/1992 |
| WO | 9207076 | A1 | 4/1992 |
| WO | 1992006204 | | 4/1992 |
| WO | 1992011272 | | 7/1992 |
| WO | 9214843 | A1 | 9/1992 |
| WO | 9216221 | A1 | 10/1992 |
| WO | 9218619 | A1 | 10/1992 |
| WO | 1992020791 | A1 | 11/1992 |
| WO | 9308278 | A1 | 4/1993 |

(56) References Cited

FOREIGN PATENT DOCUMENTS

| | | | |
|---|---|---|---|
| WO | 1993006213 | A1 | 4/1993 |
| WO | 1993011236 | A1 | 6/1993 |
| WO | 1993019172 | A1 | 9/1993 |
| WO | 9406498 | A1 | 3/1994 |
| WO | 9408552 | A2 | 4/1994 |
| WO | 9416970 | A1 | 8/1994 |
| WO | 1994018219 | | 8/1994 |
| WO | 9425585 | A1 | 11/1994 |
| WO | 1995001438 | | 1/1995 |
| WO | 9516027 | A1 | 6/1995 |
| WO | 1995015388 | | 6/1995 |
| WO | 9607754 | A1 | 3/1996 |
| WO | 9613583 | A2 | 5/1996 |
| WO | 9619256 | A1 | 6/1996 |
| WO | 9633735 | | 10/1996 |
| WO | 9634096 | A1 | 10/1996 |
| WO | 9708320 | A1 | 3/1997 |
| WO | 9713852 | A1 | 4/1997 |
| WO | 9715327 | | 5/1997 |
| WO | 9722376 | A1 | 6/1997 |
| WO | 1997020032 | | 6/1997 |
| WO | 9725086 | | 7/1997 |
| WO | 1998001757 | | 1/1998 |
| WO | 9824884 | A1 | 6/1998 |
| WO | 9824893 | A1 | 6/1998 |
| WO | 9835888 | A1 | 8/1998 |
| WO | 9850433 | A2 | 11/1998 |
| WO | 9853847 | A1 | 12/1998 |
| WO | 1999006834 | | 2/1999 |
| WO | 9937682 | | 7/1999 |
| WO | 9954342 | A1 | 10/1999 |
| WO | 0034459 | | 6/2000 |
| WO | 0056772 | | 9/2000 |
| WO | 0119373 | | 3/2001 |
| WO | 200212500 | | 2/2002 |
| WO | 03011878 | A2 | 2/2003 |
| WO | 2006028936 | A2 | 3/2006 |
| WO | 2007077217 | | 7/2007 |
| WO | 2010136492 | | 12/2010 |
| WO | 2011017294 | | 2/2011 |
| WO | 2011131746 | A2 | 10/2011 |
| WO | 2012120500 | | 9/2012 |
| WO | 2013009535 | | 1/2013 |
| WO | 2015128314 | | 9/2015 |
| WO | 2016061424 | | 4/2016 |
| WO | 2016089919 | | 6/2016 |
| WO | 2017033121 | A1 | 3/2017 |
| WO | 2017079116 | | 5/2017 |
| WO | 2017136524 | | 8/2017 |
| WO | 2017186671 | | 11/2017 |
| WO | 2018024770 | A1 | 2/2018 |
| WO | 2018140121 | | 8/2018 |
| WO | 2020142275 | | 7/2020 |
| WO | 2020183269 | | 9/2020 |
| WO | 2020183270 | | 9/2020 |
| WO | 2020183271 | | 9/2020 |
| WO | 2020183418 | | 9/2020 |

OTHER PUBLICATIONS

A. U. Gubler et al (Coexpression of Two Distinct Genes is Required to Generate Secreted Bioactive Cytotoxic Lymphocyte Maturation Factor) Proc. Natl. acad. Sci. USA. vol. 88. pp. 4143-4147—(May 1991) Immunology.

Aggarwal, et al., "Interleukin-23 Promotes a Distinct CD4 T Cell Activation State characterized by the Production of Interleukin-17," The Journal of Biological Chemistry, 278(3): 1910-1914 (2003).

Aggeletopoulou I, et al. "Interleukin 12/interleukin 23 pathway: Biological basis and therapeutic effect in patients with Crohn's disease." World J Gastroenterol. 2018;24(36):4093-4103.

Alt, et al., "Selective Multiplication of Dihydrofolate Reductase Genes in Methotrexate-resistant Variants of Cultured Murine Cells", Journal of Biological Chemistry, vol. 253 (1978), pp. 1357-1370.

Alvin S. Stern et al—(Purification to Homogeneity and Partial Characterization of Cytotoxic Lymphocyte Maturation Factor From Human B-Lymphoblastoid Cells) (Jun. 11, 1990) F. Hoffmann La Roche Inc. Nutley NJ USA. Proc. National Acad. Sci. USA (vol. 87, pp. 6808-6812—Sep. 1990—Immunology).

Annalisa D'Andrea et al. (Production of Natural Killer Cell Stimulatory Factor (Interleukin 12) by Peripheral Blood Mononuclear Cell) J. Exp. Med. The Rockefeller university press—0022-1007/92/11/1387 vol. 176 Nov. 1992. pp. 1387-1398.

Babcook et al., "A novel strategy for generating monoclonal antibodies from single, isolated lymphocytes producing antibodies of defined specificities", Proc. Natl. Acad. Sci. USA, vol. 93 (1996), pp. 7843-7848.

Beck et al., "Strategies and challenges for the next generation of therapeutic antibodies." Nature Reviews Immunology, vol. 10, No. 5 (2010), pp. 345-352.

Boshart, et al., "A Very Strong Enhancer Is Located Upstream of an Immediate Early Gene of Human Cytomegalovirus", Cell, vol. 41 (1985), pp. 521-530.

Carter, et al., "Humanization of an anfi-pISS™12 antibody for human Cancer therapy," Proceedings of the National Academy of Science USA, 89: 4285-4289 (1992).

Carter, et al., "Production and Characterization of Monoclonal Antibodies to Human Interleukin-12," Hybridoma, 16(4): 363-369 (1997).

Casipit, et al., "Improving the binding affinity of an antibody using molecular modeling and site-directed mutagenesis," Protein Science, 7: 1671-1680 (1998).

Chothia, et al., "Canonical Structures for the Hypervariable Regions of Immunoglobulins", Journal of Molecular Biology, vol. 196 (1987), pp. 901-917.

Chung, C. H. et al., "Cetuximab-Induced Anaphylaxis and IgE Specific for Galactose-a-1,3-Galactose", N Eng J Med, vol. 358, No. 11 (2008), pp. 1109-1117.

Conrad et al., "Compartment-specific accumulation of recombinant immunoglobulins in plant cells: an essential tool for antibody production and immunomodulation of physiological functions and pathogen activity", Plant Molecular Biology, vol. 38 (1998), pp. 101-109.

Cramer et al., "Transgenic Plants for Therapeutic Proteins: Linking Upstream and Downstream Strategies", Current Topics in Microbiology and Immunology, vol. 240 (1999), pp. 95-118.

Cullen, et al., "Functional Analysis of the Transcription Control Region Located Within the Avian Retroviral Long Terminal Repeat", Molecular and Cellular Biology, vol. 5 (1985), pp. 438-447.

Dai, J., et al. "Capillary Isoelectric Focusing-Mass Spectrometry Method for the Separation and Online Characterization of Intact Monoclonal Antibody Charge Variants", Anal. Chem, vol. 90, No. 3 (2018), pp. 2246-2254.

Dai, J., et al., "Essential roles of IL-12 and dendritic cells but not IL-23 and macrophages in lupus-like diseases initiated by cell surface HSP gp96", European Journal of Immunology, vol. 37, No. 3 (2007), pp. 706-715.

Davidson, et al., "IL-12, But Not IFN-y, Plays a Major Role in Sustaining the Chronic Phase of Colitis inIL-10-DeficientMice," The Journal of Immunology, 161: 3143-3149 (1998).

Dolinar, et al., "A Guide to Follow-On Biologics and Biosimilars With a Focus on Insulin." Endocrine Practice, vol. 24, No. 2, pp. 195-204, (Feb. 2018).

Eduardo Padlan, "Anatomy of the Antibody Molecule," Molecular Immunology, 31(3): 169-217 (1994).

Elliott, M.J. et al., "A Repeated Therapy with Monoclonal Antibody to Tumour Necrosis Factor a (cA2) in Patients with Rheumatoid Arthritis", The Lancet, vol. 344 (1994), pp. 1125-1127.

Eren et al. "Human monoclonal antibodies specific to hepatitis B virus generated in a human/mouse radiation chimera: the Trimera system", Immunology, vol. 93 (1998), pp. 154-161.

Fischer et al., "Towards molecular farming in the future: moving from diagnostic protein and antibody production in microbes to plants", Biotechnology and Applied Biochemistry, vol. 30 (1999), pp. 101-108.

(56) References Cited

OTHER PUBLICATIONS

Fishwild et al., "High-avidity human IgGk monoclonal antibodies from a novel strain of minilocus transgenic mice", Nature Biotechnology, vol. 14, No. 7 (1996), pp. 845-851.
Geist, B. J., et al. "A Novel Approach for the Simultaneous Quantification of A Therapeutic Monoclonal Antibody in Serum Produced from Two Distinct Host Cell Lines", mAbs, vol. 5, No. 1 (2012), pp. 150-161.
Ghaderi et al., "Implications of the presence of N-glycolylneuraminic acid in recombinant therapeutic glycoproteins." Nature Biotechnology, vol. 28, No. 8 (2010), pp. 863-867.
Giorgetti, J., et al. "Monoclonal Antibody N-Glycosylation Profiling Using Capillary Electrophoresis-Mass Spectrometry: Assessment and Method Validation", Talanta, vol. 178 (2018), pp. 530-537.
Goetze et al., "High-mannose glycans on the Fc region of therapeutic IgG antibodies increase serum clearance in humans." Glycobiology, vol. 21, No. 7 (2011), pp. 949-959.
Gossen, and H. Bujard, "Tight control of gene expression in mammalian cells by tetracycline-responsive promotoers", Proc. Natl. Acad. Sci. USA, vol. 89 (1992), pp. 5547-5551.
Gray et al., "Secretion capture and report web: use of affinity derivatized agarose microdroplets for the selection of hybridoma cells", Journal of Immunological Methods, vol. 182 (1995), pp. 155-163.
Green et al, "Antigen-specific human monoclonal antibodies from mice engineered with human Ig heavy and light chain YACs", Nature Genetics, vol. 7 (1994), pp. 13-21.
Hanes et al. "Ribosome display efficiently selects and evolves high-affinity antibodies in vitro from immune libraries", Proc Natl. Aca. Sci USA, vol. 95 (1998), pp. 14130-14135.
Hanes et al., "In vitro selection and evolution of functional proteins by using ribosome display", Proc. Natl. Acad. Sci. USA, vol. 94 (1997), pp. 4937-4942.
Hodoniczky et al., "Control of recombinant monoclonal antibody effector functions by Fc N-glycan remodeling in vitro." Biotechnology Progress, vol. 21 (2005), pp. 1644-1652.
Hong, et al., IL-12, independently of IFN-gamma, plays a crucial role in the pathogenesis of a murine psoriasis-like skindisorder, Journal of Immunology, 162(12): 7480-7491 (1999).
Hood et al., "Molecular Farming of Industrial Proteins from Transgenic Maize", Advances in Experimental Medicine and Biology, vol. 464 (1999), pp. 127-147.
J. L. Hamlin and C. Ma, "The mammalian dihydrofolate reductase locus", Biochimica et Biophysica Acta, vol. 1097 (1990), pp. 107-143.
Jayanthi S, et al. "Modulation of Interleukin-12 activity in the presence of heparin." Sci Rep. 2017; 7(1): 5360.
Jones, et al., "Replacing the complementarity-determining regions in a human antibody with those from a mouse," Nature, vol. 321 (1986), pp. 522-525.
Katsube, Y., et al., "Analysis of k light chain contribution to anti-DNA antibody activity of a human VH4-21-encoded monoclonal antibody (NE-1) by antibody-phage display technique", International Journal of Molecular Medicine, vol. 1, No. 5 (1998), pp. 863-868.
Kenny et al., "Production of Monoclonal Antiboodies Using a Secretion Capture Report Web", Bio/Technology, vol. 13 (1995), pp. 787-790.
Kikawada et al, "IL-12 Deficiency in MRL-Faslpr Mice Delays Nephritis and Intrarenal IFN-γ Expression, and Diminishes Systemic Pathology." Journal of Immunology, vol. 170, No. 7 (2003), pp. 3915-3925.
Kunert et al. Advances in recombinant antibody manufacturing : Appl. Micorbiol. Biotechnol. 100:3451-3461, 2016.
Langrish, et al., "IL-23 drives a pathogenic T cell population that induces autoimmune inflammation," Journal of Experimental Medicine, 201(20: 233-240 (2005).
Leonard, et al., "Prevention of experimental autoimmune encephalomyelitis by antibodies against interleukin 12," Journal of Experimental Medicine, 181(1): 381-386 (1995).
Liming Liu, "Antibody Glycosylation and Its Impact on the Pharmacokinetics and Pharmacodynamics of Monoclonal Antibodies and Fc-Fusion Proteins." Journal of Pharmaceutical Sciences, 104(6), Jun. 2015, pp. 1866-1884.
Lonberg et al. "Antigen-specific human antibodies from mice comprising four distinct genetic modifications", Nature, vol. 368 (1994), pp. 856-859.
Lonberg et al., "Human Antibodies from Transgenic Mice", International Reviews of Immunology, vol. 13, No. 1 (1995), pp. 65-93.
M. Gately et al. (Regulation of Human Lymphocyte Proliferation by a Heterodimeric Cytokine IL-12 (Cytotoxic Lymphocyte Maturation Factor) vol. 147—874-882 No. 3. (Aug. 1, 1991). (The Journal of Immunology).
M. J. Page and M. A. Sydenham, "High Level Expression of the Humanized Monoclonal Antibody Campath-1H in Chinese Hamster Ovary Cells", Biotechnology, vol. 9 (1991), pp. 64-68.
Ma et al., "Immunotherapeutic potential of antibodies produced in plants", Trends in Biotechnology, vol. 13 (1995), pp. 522-527.
Ma et al., "Plant Antibodies for Immunotherapy", Plant Physiology, vol. 109 (1995), pp. 341-346.
Malfait, et al., "Blockade of IL-12 during the induction of collagen-induced arthritis (CIA) markedly attenuates the severity of the arthritis," Clinical and Experimental Immunology, 111:327-383 (1998).
Markus F. Neurath et al. (Antibodies to Interleukin 12 Abrogate Established Experimental Colitis in Mice) The Journal of Experimental Medicine—vol. 182—Nov. 1995—pp. 1281-1290.
Matsumiya et al., "Structural comparison of fucosylated and nonfucosylated Fc fragments of human immunoglobulin G1." Journal of Molecular Biology, vol. 368 (2007), pp. 767-779.
Mendez, et al., "Functional transplant of megabase human immunoglobulin loci recapitulates human antibody response in mice," Nature Genetics, vol. 15, No. 2 (1997), pp. 146-156.
Michiko Kobayashi et al. I ( Identification and Purification of Natural Killer Cell Stimulatory Factor (NKSF) a Cytokine With Multiple Biologic Efects on Human Lymphocytes) J. Exp. Med. The Rockefeller university Press—vol. 170—(Sep. 1989) pp. 827-845.
Milstein, et al., "Hybrid hybridomas and their Use in Immunohistochemistry," Nature, vol. 305 (1983), pp. 537-540.
Nguyen et al., "Production of Human Monoclonal Antibodies in SCID Mouse", Microbiology and Immunology, vol. 41 (1997), pp. 901-907.
Nicolas M. Valiante et al. ( Role of the Production of Natural Killer Cell Stimulatory Factor (NKSF/IL-12) in the Ability of B Cell Lines to Stimulate T and NK Cell Proliferation). Cellunar Immunology 145, 187-198-(1992).
Nikhil, Yawalkar et al.; "Expression of interleukin-12 is increased in psoriatic skin", Journal of Investigative Dermatology, Dec. 1998, pp. 1053-1057; vol. 111, No. 6; XP00800577; ISSN: 0022-202X, abstract.
Office Action (Non-Final Rejection) dated Mar. 9, 2023 for U.S. Appl. No. 16/816,814 (pp. 1-13).
Onitsuka, M., et al., "Glycosylation analysis of an aggregated antibody produced by Chinese hamster ovary cells in bioreactor culture", Journal of Bioscience and Bioengineering, vol. 117, No. 5 (2014), pp. 639-644.
Oppmann, et al., "Novel p19 Protein Engages IL-12p40 to Form a Cytokine, IL-23, with Biological Activities Similar as Well as Distinct from IL-12," Immunity, 13: 715-725 (2000).
Parham, et al., "A Receptor for the Heterodimeric Cytokine IL-23 is Composed of IL-12R□ 1 and a Novel Cytokine Receptor Subunit, IL-23R," The Journal of Immunology, 168: 5699-5708 (2002).
PCT International Search Report PCT/US01/24720 dated Jul. 30, 2002, 9 pages.
Powell et al., "Gel Microdroplets and Flow Cytometry: Rapid Determination of Antibody Secretion by Individual Cells Within a Cell Population", Biotechnology, vol. 8 (1990), pp. 333-337.
Presky et al., "A functional interleukin 12 receptor complex is composed of two beta-type cytokine receptor subunits," Proceedings of the National Academy of Science USA, 93(24): 14002-14007 (1996).
Presta, et al., "Humanization of an antibody y directed against IgE," Journal of Immunology, 151: 2623-2632 (1993).

(56) References Cited

OTHER PUBLICATIONS

R. Chizzonite et al. (IL-12 Monoclonal Antibodies Specific for the 40-KdA Subunit Block Receptor Binding and Biologic Activity on Activated Human Lymphoblasts.) vol. 147, 1548-1556—No. 5, (Sep. 1, 1991) The Journal of Immunology.
R.W. Carter et al. (Production and Characterization of Monoclonal Antibodies to Human Interleukin-12) Hybriidona 16: 363-369 (1997).
Rainer Duchmann et al. ( Tolerance Towards Resident Intestinal Flora in Mice is Abrogated in Experimental Colitis and Restores by Treatment With Intelukin-1 or Antibodies to Interleukin-12) European Journal of Immunology, 26: 394-938 (1996).
Riechmann, et al., "Reshaping human antibodies for therapy," Nature, vol. 332 (1988), pp. 323-327.
Romagnani, et al., "T cells and cytokines in Crohn's Disease," Current Opinion in Immunology, 9: 793-799 (1997).
Sandhu et al., "The Use of SCID Mice in Biotechnology and as a Model for Human Disease", Critical Reviews in Biotechnology, vol. 16 (1996), pp. 95-118.
Scallon, B. J., et al., "Higher levels of sialylated Fc glycans in immunoglobulin G molecules can adversly impact functionality", Mol Immunol, vol. 44, No. 7 (2007), pp. 1524-1534.
Schildbach, et al., "Modulation of antibody affinity by a non-contact residue," Protein Science, 2: 206-214 (1993).
Schwaigerlehner et al., "Germinality does not necessarily define mAb expression and thermal stability." Applied Microbiology and Biotechnology, Springer Berlin Heidelberg, vol. 103, No. 18, Jul. 26, 2019, pp. 7505-7598.
Schwaigerlehner, L. "Antibody Gene Expression in CHO cells with recombinase mediated cassette exchange", University of Natural Resources and Life Sciences Master Thesis (2015). 105 pages.
Shade and Anthony, "Antibody Glycosylation and Inflammation." Antibodies, vol. 2, No. 3 (2013), pp. 392-414.
Shields et al., "Lack of Fucose on Human IgG1 N-Linked Oligosaccharide Improves Binding to Human FcyRIII and Antibody-dependent Cellular Toxicity*". J Biol Chem, 2002, pp. 26733-26740, vol. 277(30).
Shields, et al., "High Resolution Mapping of the Binding Site onHuman IgFI for FOyRI, FCyRII, FCyRIII, and RcRn and Design of IgGI Variants with Improved Binding to the RCyR," The Journal of Biological Chemistry, 276(9): 6591-6604 (2001).
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity*. ", J Biol Chem, 2003, pp. 3466-3473, vol. 278(5).
Siemiatkoski J, et al. Glycosylation of Therapeutic Proteins: Current Understanding of Structure-Function Relationships. BioProcess International, vol. 9, No. 6 (2011), pp. 48-53.
Sims et al., "A Humanized CD18 Antibody Can Block Function without Cell Destruction", Journal of Immunology, vol. 151 (1993), p. 2296.
Sprague, et al., "Expression of a Recombinant DNA Gene Coding for the Vesicular Stomatitis Virus Nucleocapsid Protein", Journal of Virology, vol. 45 (1983), pp. 773-781.
Steenbakkers et al., "Efficient generation of monoclonal antibodies from preselected antigen-specific B", Molecular Biology Reports, vol. 19 (1994), pp. 125-134.
Susan H. Chan et al. (Introduction of Interferon Production by Natural Killer Cell Stimulatory Factor Characterization of the Responder Cells and Synergy With Other Inducers) (The Rockefeller University Press)—0022-1007/91/04/0869/—vol. 173 Apr. 1991—pp. 869-879.
Sylvie Trembleau et al. (The Role of IL-12 in the Induction of Organ-Specific Autoimmune Diseases), Immunology Today, 16(8): 383-386 (1995).
Taylor et al., "A transgenic mouse that expresses a diversity of human sequence heavy and light chain immunoglobulins", Nucleic Acids Research, vol. 20, No. 23 (1992), pp. 6287-6295.
Taylor, et al., "Human immunoglobulin transgenes undergo rearrangement, somatic mutation and class switching in mice that lack endogenous IgM," International Immunology, vol. 6, No. 4 (1994), pp. 579-591.
Trinchieri, et al., "The IL-12 Family of Heterodimeric Cytokines: New Players in the Regulation of T Cell Responses," Immunity, 19: 641-644 (2003).
Tuaillon et al., "Human immunoglobulin heavy-chain minilocus recombination in transgenic mice: Gene-segment use in u and y transcripts", Proc Natl Acad Sci USA, vol. 90, No. 8 (1993), pp. 3720-3724.
Umana, et al., "Engineered glycoforms of an anfineuro-blastoma IgGI with optimized antibody-dependent cellular cytotoxic activity," Nature Biotechnology, 17: 176-190 (1999).
Verhoeyen et al., "Reshaping Human Antibodies: Grafting an Antilysozyme Activity", Science, vol. 239 (1988), p. 1534.
Wen et al., "Limiting diluation assay for human B cells based on their activation by mutant EL4 thymoma cells:total and antimalaria responder B cell frequencies" Journal of Immunology, vol. 17 (1987), pp. 887-892.
"Jayapal et al., "Recombinant protein therapeutics from CHO cells—20 years and counting", Chemical Engineering Progress, vol. 103 (2007), pp. 40-47."
Anthony Lubiniecki et al, "Comparability assessments of process and product changes made during development of two different monoclonal antibodies", Aug. 27, 2010 (Aug. 27, 2010), vol. {0} 39, No. {0} 1, p. 9-22.
Ashkenazi et al., 1991, "Protection against endotoxic shock by a tumor necrosis factor receptor immunoadhesin," Proc. Natl. Acad. Sci. USA, 88(23): 10535-10539.
Baker et al., "Control of established experimental allergic encephalomyelitis by inhibition of tumor necrosis factor (TNF) activity within the central nervous system using monoclonal antibodies and TNF receptor-immunoglobulin fusion proteins", European Journal of Immunology, vol. 24 (1994), pp. 2040-2048.
Bebbington, et al., "High-Level Expression of a Recombinant Antibody from Myeloma Cells Using a Glutamine Systhetase Gene as an Amplifiable Selectable Marker", Bio/Technology, vol. 10 (1992), pp. 169-175.
Bellinvia S, Cummings JRF, Ardern-Jones MR, Edwards CJ. Adalimumab Biosimilars in Europe: An Overview of the Clinical Evidence. BioDrugs. Jun. 2019;33(3):241-253.
Biotechnology & genetic engineering reviews, Stephenomenon E. Harding, Nottingham University Press, pp. 11-12, Dec. 31, 2010.
Bringman, Timothy S. and Aggarwal, Bharat B., "Monoclonal Antibodies to Human Tumor Necrosis Factors Alpha and Beta: Applications for Affinity Purification, Immunoassays, and as Structural Probes," Hybridoma, vol. 6, No. 5 (1987), pp. 489-507.
Butler et al., "TNF Receptor Fusion Proteins Are Effective Inhibitors of TNF-Mediated Cytotoxicity on Human KYM-1D4 Rhabdomyosarcoma Cells", Cytokine, vol. 6, No. 6 (1994), pp. 616-623.
Capellas, et al., "Enzymatic Condensation of Cholecystokinin CCK-8 (4-6) and CCK-8 (7-8) Peptide Fragments in Organic Media," Biotechnology and Bioengineering, vol. 56, No. 4 (1997), pp. 456-463.
Capon et al., "Designing CD4 immunoadhesins for AIDS therapy", Nature, vol. 337 (1989), pp. 525-531.
Caron AL, Biaggio RT, Swiech K. Strategies to Suspension Serum-Free Adaptation of Mammalian Cell Lines for Recombinant Glycoprotein Production. Methods Mol Biol. 2018;1674:75-85.
Carter et al., "Humanization of an anti-p185HER2 antibody for human cancer therapy", Proc. Natl. Acad. Sci. U.S.A., vol. 89 (1992), p. 4285.
Chen, Hongxia et al., "Development of a method for detection of serum neutralizing antibodies in cynomolgus monkeys undergoing repeated dose toxcity study of humanized anti-TNF-alpha monoclonal antibody WLB303", Chinese Journal of New Drugs. 2017. vol. 26, No. 20. pp. 2386-2395.
Corcoran et al., "Characterization of ligand binding by the human p55 tumour-necrosis-factor receptor", European Journal of Biochemistry, vol. 223 (1994), pp. 831-840.

(56) References Cited

OTHER PUBLICATIONS

Crowell CK, Grampp GE, Rogers GN, Miller J, Scheinman RI. Amino acid and manganese supplementation modulates the glycosylation state of erythropoietin in a CHO culture system. Biotechnol Bioeng. Feb. 15, 2007;96(3):538-49.
Crowell et al., "Amino acid and manganese supplementation modulates the glycosylation state of erythropoietin in a CHO culture system" Biotechnology and Bioengineering, vol. 96, No. 3 (2007), pp. 538-549.
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.
De Vos, et al., "Human Growth Hormone and Extracellular Domain of Its Receptor: Crystal Structure of the Complex", Science, vol. 255 (1992), pp. 306-312.
Endrenyi, L., Declerck, D.P., & Chow, S.-C. (Eds.). (2017). Biosimilar Drug Product Development (1st ed.). CRC Press. 4 pages.
Engelmann, Hartmut et al., "Two Tumor Necrosis Factor-binding Proteins Purified from Human Urine," Journal of Biological Chemistry, vol. 265, No. 3 (1990), pp. 1531-1536.
Fendly, Brian M. et al., "Murine Monoclonal Antibodies Defining Neutralizing Epitopes on Tumor Necrosis Factor," Hybridoma, vol. 6, No. 4 (1987), pp. 359-370.
Fisch et al., "Site-Specific Modification of a Fragment of a Chimeric Monoclonal Antibody Using Reverse Proteolysis", Bioconjugate Chemistry, vol. 3 (1992), pp. 147-153.
Gervais, D. Protein deamidation in biopharmaceutical manufacture: understanding, control and impact, J. Chem. Technol. Biotechnol., 2015, 91 , 569-575 published Nov. 17, 2015 (Year: 2015).
Goel et al. Plasticity within the Antigen-Combining Site May Manifest as Molecular Mimicry in the Humoral Immune Response. 1 J. Immunol. 173(12)7358-7367, 2004.
Haga, Yoshimi, et al. "Fast and Ultrasensitive Glycoform Analysis by Supercritical Fluid Chromatography—Tandem Mass Spectrometry." Analytical Chemistry 94.46 (2022): 15948-15955.
Hirai, Makoto et al., "Production and characterization of monoclonal antibodies to human tumor necrosis factor," Journal of Immunological Methods, vol. 96 (1987), pp. 57-62.
Itoh et al., "Application of Inverse Substrates to Trypsin-Catalyzed Peptide Synthesis", Bioorganic Chemistry, vol. 24, No. 1 (1996), pp. 59-68.
Kahn et al. Adjustable Locks and Flexible Keys: Plasticity of Epitope-Paratope Interactions in Germline Antibodies. J. Immunol. 192:5398-5405, 2014.
Kaschak T, Boyd D, Lu F, Derfus G, Kluck B, Nogal B, Emery C, Summers C, Zheng K, Bayer R, Amanullah A, Yan B. Characterization of the basic charge variants of a human IgG1: effect of copper concentration in cell culture media. MAbs. Nov.-Dec. 2011;3(6):577-83.
Kato Koichi et al, "Mechanisms of Deamidation of Asparagine Residues and Effects of Main-Chain Conformation on Activation Energy", Sep. 24, 2020 (Sep. 24, 2020), vol. {0} 21, No. {0} 19, p. 7035.
Kolls et al., "Prolonged and effective blockade of tumor necrosis factor activity through adeno virus-mediated gene transfer", Proc. Natl. Acad. Sci. USA, vol. 91 (1994), pp. 215-219.
Kumaran et al., "Conformationally driven protease-catalyzed splicing of peptide segments: V8 protease-mediated synthesis of fragments derived from thermolysin and ribonuclease A", Protein Science, vol. 6, No. 10 (1997), pp. 2233-2241.
Lee et al., "Glycosylation profile and biological activity of Remicade® compared with Flixabi® and Remsima®", MAbs, vol. 9, No. 6 (2017), pp. 968-977.
Lesslauer et al., "Recombinant soluble tumor necrosis factor receptor proteins protect mice from lipopolysaccharide-induced lethality", European Journal of Immunology, vol. 21 (1991), pp. 2883-2886.
Liang, Chi-Ming et al., "Production and Characterization of Monoclonal Antibodies Against Recombinant Human Tumor Necrosis Factor/Cachectin," Biochemistry & Biophysics Research Communication, vol. 137, No. 2 (1986), pp. 847-854.
Liming Liu, "Antibody Glycosylation and Its Impact on the Pharmacokinetics and Pharmacodynamics of Monoclonal Antibodies and Fc-Fusion Proteins", Journal of Pharmaceutical Sciences, vol. {0} 104, No. {0} 6, Jun. 1, 2015 (Jun. 1, 2015), p. 1866-1884.
Liu Tao et al, "Identification, Efficacy, and Stability Evaluation of Succinimide Modification With a High Abundance in the Framework Region of Golimumab", Apr. 5, 2022 (Apr. 5, 2022), vol. {0} 10.
Loetscher et al., "Molecular Cloning and Expression of the Human 55 kd Tumor Necrosis Factor Receptor", Cell, vol. 61 (1990), pp. 351-359.
Maccallum et al. "Antibody-antigen interactions: contact analysis and binding site topography", Journal of Molecular Biology, 1996. vol. 262, pp. 732-745.
Manning MC, Patel K, Borchardt RT. Stability of protein pharmaceuticals. Pharm Res. Nov. 1989;6(11):903-18.
Markert S, Torkler S, Hohmann K, Popp O. Traces matter: Targeted optimization of monoclonal antibody N-glycosylation based on/by implementing automated high-throughput trace element screening. Biotechnol Prog. Nov. 2020;36(6):e3042.
Marrack et al, "The Staphylococcal Enterotoxins and Their Relatives", Science, vol. 248 (1990), pp. 705-711.
Meager, Anthony et al., "Preparation and Characterization of Monoclonal Antibodies Directed Against Antigenic Determinants of Recombinant Human Tumour Necrosis Factor (rTNF)," Hybridoma, vol. 6, No. 3 (1987), pp. 305-311.
Mitoma H, Horiuchi T, Tsukamoto H, Ueda N. Molecular mechanisms of action of anti-TNF-αagents—Comparison among therapeutic TNF-α antagonists. Cytokine. Jan. 2016;101:56-63.
Moller, Achim et al., "Monoclonal Antibodies to Human Tumor Necrosis Factor a: In Vitro and In Vivo Application," Cytokine, vol. 2, No. 3 (1990), pp. 162-169.
Murphy, et al., "Matrix metalloproteinase degradation of elastin, type IV collagen and proteoglycan", Biochem. J., vol. 277 (1991), pp. 277-279.
Neuberger, M., "Generating high-avidity human Mabs in mince", Nature Biotechnology, vol. 14 (1996), p. 826.
Park et al., "Expression and characterization of beta-1,4-galactosyltransferase from Neisseria meningitidis and Neisseria gonorrhoeae." Korean Society for Biochemistry and Molecular Biology, vol. 35, No. 3 (2002), pp. 330-336.
Park JE, Lee KY, Do SI, Lee SS. Expression and characterization of beta-1,4-galactosyltransferase from Neisseria meningitidis and Neisseria gonorrhoeae. J Biochem Mol Biol. May 31, 2002;35(3):330-6.
Peppel et al., "A Tumor Necrosis Factor (TNF) Receptor-IgG Heavy ChainChimeric Protein as a Bivalent Antagonist of TNF Activity", Journal of Experimental Medicine, vol. 174 (1991), pp. 1483-1489.
Poosarla et al. Computational De Novo Design of Antibodies Binding to a Peptide With High Affinity. Biotech. Bioeng. 114(6): 1331-1342, 2017.
Popp, O. et al., "Development of a pre-glycoengineered CHO-K1 host cell line for the expression of antibodies with enhanced Fc mediated effector function", MABS, 10, pp. 290-303, 2018.
Qasba et al., "Structure and function of beta-1,4-galactosyltransferase." Current Drug Targets, vol. 9, No. 4 (2008), pp. 292-309.
Qasba PK, Ramakrishnan B, Boeggeman E. Structure and function of beta-1,4-galactosyltransferase. Curr Drug Targets. Apr. 2008;9(4):292-309.
Qingrong Yan et al, "Structure Based Prediction of Asparagine Deamidation Propensity in Monoclonal Antibodies", MAbs. Aug./Sep. 2018;10(6): 901-912.
Scallon, et al., "Functional Comparisons of Different Tumour Necrosis Factor Receptor/IgG Fusion Proteins", Cytokine, vol. 7 (1995), pp. 759-770.
Schall, Thomas J. et al., "Molecular Cloning and Expression of a Receptor for Human Tumor Necrosis Factor," Cell, vol. 61 (1990), pp. 361-370.
Simonov V, Ivanov S, Smolov M, Abbasova S, Piskunov A, Poteryaev D. Control of therapeutic IgG antibodies galactosylation

(56) References Cited

OTHER PUBLICATIONS during cultivation process and its impact on IgG1/FcγR interaction and ADCC activity. Biologicals. Mar. 2019;58:16-21.
Smith, et al., “Human Interleukin 4: The Solution Structure of a Four-helix Bundle Protein”, Journal of Molecular Biology, vol. 224 (1992), pp. 899-904.
T. Horiuchi et al, “Transmembrane TNF-: structure, function and interaction with anti-TNF agents”, Rheumatology, vol. {0} 49, No. {0} 7, Mar. 1, 2010 (Mar. 1, 2010), p. 1215-1228.
Tharmala Tharmalingam et al, “A framework for real-time glycosylation monitoring (RT-GM) in mammalian cell culture”, Biotechnology and Bioengineering, John Wiley, Hoboken, USA, vol. {0} 112, No. {0} 6, Apr. 17, 2015 (Apr. 17, 2015), p. 1146-1154.
Torkashvand, F., et al., “Main Quality Attributes of Monoclonal Antibodies and Effect of Cell Culture Components,” Iranian Biomedical Journal, vol. 21, No. 3 (2017), pp. 131-141.
Voorter CE, de Haard-Hoekman WA, van den Oetelaar PJ, Bloemendal H, de Jong WW. Spontaneous peptide bond cleavage in aging alpha-crystallin through a succinimide intermediate. J Biol Chem. Dec. 15, 1988;263(35):19020-3.
Werlen et al., “Site-Specific Conjugation of an Enzyme and an Antibody Fragment”, Bioconjugate Chemistry, vol. 5 (1994), pp. 411-417.
Wood et al, “Staphylococcal enterotoxins and the immune system”, FEMS Microbiology Immunology, vol. 76 (1991), pp. 121-134.
Yuk et al. Effects of copper on CHO cells: Cellular requirements and product quality considerations. Biotechnol Progress, 2015, 31: 226-238. (Year: 2015).

Overview of Manufacturing Process - Process Stages

Stage 1 Process Flow Diagram for Preculture and Expansion of Cells

Stage 2 Process Flow Diagram

Representative HPLC Chromatogram for Oligosaccharide Analysis of Ustekinumab Produced in Sp2/0 Cells

Representative Deconvoluted Mass Spectrum for IRMA Analysis of Ustekinumab Produced in Sp2/0 Cells

Representative cIEF Electropherogram Profile for Ustekinumab Produced in Sp2/0 cells

Diagram of primary N-linked oligosaccharide species in Ustekinumab IgG

Representative HPLC Chromatogram for Oligosaccharide Analysis of Ustekinumab Produced in CHO Cells

Representative cIEF Electropherogram Profile for Ustekinumab Produced in CHO cells

SEQUENCE LISTING

```
Sequence total quantity: 11
SEQ ID NO: 1            moltype = AA  length = 5
FEATURE                 Location/Qualifiers
source                  1..5
                        mol_type = protein
                        organism = Homo sapiens

SEQUENCE: 1
TYWLG                                                              5

SEQ ID NO: 2            moltype = AA  length = 17
FEATURE                 Location/Qualifiers
source                  1..17
                        mol_type = protein
                        organism = Homo sapiens

SEQUENCE: 2
IMSPVDSDIR YSPSFQG                                                 17

SEQ ID NO: 3            moltype = AA  length = 10
FEATURE                 Location/Qualifiers
source                  1..10
                        mol_type = protein
                        organism = Homo sapiens

SEQUENCE: 3
RRPGQGYFDF                                                         10

SEQ ID NO: 4            moltype = AA  length = 11
FEATURE                 Location/Qualifiers
source                  1..11
                        mol_type = protein
                        organism = Homo sapiens

SEQUENCE: 4
RASQGISSWL A                                                       11

SEQ ID NO: 5            moltype = AA  length = 7
FEATURE                 Location/Qualifiers
source                  1..7
                        mol_type = protein
                        organism = Homo sapiens

SEQUENCE: 5
```

-continued

```
AASSLQS                                                  7

SEQ ID NO: 6           moltype = AA  length = 9
FEATURE                Location/Qualifiers
source                 1..9
                       mol_type = protein
                       organism = Homo sapiens
SEQUENCE: 6
QQYNIYPYT                                                9

SEQ ID NO: 7           moltype = AA  length = 119
FEATURE                Location/Qualifiers
source                 1..119
                       mol_type = protein
                       organism = Homo sapiens
SEQUENCE: 7
EVQLVQSGAE VKKPGESLKI SCKGSGYSFT TYWLGWVRQM PGKGLDWIGI MSPVDSDIRY  60
SPSFQGQVTM SVDKSITTAY LQWNSLKASD TAMYYCARRR PGQGYFDFWG QGTLVTVSS   119

SEQ ID NO: 8           moltype = AA  length = 108
FEATURE                Location/Qualifiers
source                 1..108
                       mol_type = protein
                       organism = Homo sapiens
SEQUENCE: 8
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNIYPYTFGQ GTKLEIKR               108

SEQ ID NO: 9           moltype = AA  length = 503
FEATURE                Location/Qualifiers
source                 1..503
                       mol_type = protein
                       organism = Homo sapiens
SEQUENCE: 9
RNLPVATPDP GMFPCLHHSQ NLLRAVSNML QKARQTLEFY PCTSEEIDHE DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNASIWE LKKDVYVVEL DWYPDAPGEM VVLTCDTPEE DGITWTLDQS  240
SEVLGSGKTL TIQVKEFGDA GQYTCHKGGE VLSHSLLLLH KKEDGIWSTD ILKDQKEPKN  300
KTFLRCEAKN YSGRFTCWWL TTISTDLTFS VKSSRGSSDP QGVTCGAATL SAERVRGDNK  360
EYEYSVECQE DSACPAAEES LPIEVMVDAV HKLKYENYTS SFFIRDIIKP DPPKNLQLKP  420
LKNSRQVEVS WEYPDTWSTP HSYFSLTFCV QVQGKSKREK KDRVFTDKTS ATVICRKNAS  480
ISVRAQDRYY SSSWSEWASV PCS                                503

SEQ ID NO: 10          moltype = AA  length = 449
FEATURE                Location/Qualifiers
source                 1..449
                       mol_type = protein
                       organism = Homo sapiens
SEQUENCE: 10
EVQLVQSGAE VKKPGESLKI SCKGSGYSFT TYWLGWVRQM PGKGLDWIGI MSPVDSDIRY  60
SPSFQGQVTM SVDKSITTAY LQWNSLKASD TAMYYCARRR PGQGYFDFWG QGTLVTVSSS  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                          449

SEQ ID NO: 11          moltype = AA  length = 214
FEATURE                Location/Qualifiers
source                 1..214
                       mol_type = protein
                       organism = Homo sapiens
SEQUENCE: 11
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNIYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                     214
```

MANUFACTURING METHODS FOR PRODUCING ANTI-IL12/IL23 ANTIBODY COMPOSITIONS

CROSS-REFERENCE TO RELATED APPLICATIONS

This application is a continuation of U.S. patent application Ser. No. 16/816,814, filed Mar. 12, 2020 which claims priority to U.S. Provisional Application No. 62/818,359, filed Mar. 14, 2019, the entire contents of which are incorporated herein by reference.

REFERENCE TO SEQUENCE LISTING SUBMITTED ELECTRONICALLY

This application contains a sequence listing, which is submitted electronically via EFS-Web as an XML formatted sequence listing with a file name "206389-0051-01US_Sequence_Listing.xml" creation date of Jan. 30, 2024 and having a size of 11,969 bytes. The sequence listing is herein incorporated by reference in its entirety.

FIELD OF THE INVENTION

The present invention relates to methods of manufacture for producing anti-IL-12/IL-23p40 antibodies, e.g., the anti-IL-12/IL-23p40 antibody ustekinumab, and specific pharmaceutical compositions of the antibody.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is IL-12p35 ligation of the second receptor chain, IL-12Rβ2, that confers intracellular signaling (e.g. STAT4 phosphorylation) and activation of the receptor-bearing cell (Presky et al, 1996). IL-12 signaling concurrent with antigen presentation is thought to invoke T cell differentiation towards the T helper 1 (Th1) phenotype, characterized by interferon gamma (IFN-γ) production (Trinchieri, 2003). Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23 (Oppman et al, 2000). IL-23 also signals through a two-chain receptor complex. Since the p40 subunit is shared between IL-12 and IL-23, it follows that the IL-12Rβ1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells (Parham et al, 2002; Aggarwal et al. 2003). Recent studies have demonstrated that the biological functions of IL-23 are distinct from those of IL-12, despite the structural similarity between the two cytokines (Langrish et al, 2005).

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis (Leonard et al, 1995; Hong et al, 1999; Malfait et al, 1998; Davidson et al, 1998). IL-12 has also been shown to play a critical role in the pathogenesis of SLE in two independent mouse models of systemic lupus erythematosus (Kikawada et al. 2003; Dai et al. 2007.

Systemic lupus erythematosus (SLE) is a complex, chronic, heterogeneous autoimmune disease of unknown etiology that can affect almost any organ system, and which follows a waxing and waning disease course. Systemic lupus erythematosus occurs much more often in women than in men, up to 9 times more frequently in some studies, and often appears during the child-bearing years between ages 15 and 45. This disease is more prevalent in Afro-Caribbean, Asian, and Hispanic populations. In SLE, the immune system attacks the body's cells and tissue, resulting in inflammation and tissue damage which can harm the heart, joints, skin, lungs, blood vessels, liver, kidneys and nervous system. About half of the subjects diagnosed with SLE present with organ-threatening disease, but it can take several years to diagnose subjects who do not present with organ involvement. Some of the primary complaints of newly diagnosed lupus patients are arthralgia (62%) and cutaneous symptoms (new photosensitivity; 20%), followed by persistent fever and malaise. The estimated annual incidence of lupus varies from 1.8 to 7.6 cases per 100,000 and the worldwide prevalence ranges from 14 to 172 cases per 100,000 people. Patients with mild disease have mostly skin rashes and joint pain and require less aggressive therapy; regimens include nonsteroidal anti-inflammatory drugs (NSAIDs), anti-malarials (e.g., hydroxychloroquine, chloroquine, or quinacrine) and/or low dose corticosteroids. With more severe disease patients may experience a variety of serious conditions depending on) the organ systems involved, including lupus nephritis with potential renal failure, endocarditis or myocarditis, pneumonitis, pregnancy complications, stroke, neurological complications, vasculitis and cytopenias with associated risks of bleeding or infection. Common treatments for more severe disease include immunomodulatory agents, such as methotrexate (MTX), azathioprine, cyclophosphamide, cyclosporine, high dose corticosteroids, biologic B cell cytotoxic agents or B cell modulators, and other immunomodulators. Patients with serious SLE have a shortening of life expectancy by 10 to 30 years, largely due to the complications of the disease, of standard of care therapy, and/or accelerated atherosclerosis. In addition, SLE has a substantial impact on quality of life, work productivity, and healthcare expenditures. Existing therapies for SLE are generally either cytotoxic or immunomodulatory and may have notable safety risks. Newer treatments for SLE have provided only modest benefits over standard of care therapy. Thus, there is a large unmet need for new alternative treatments that can provide significant benefit in this disease without incurring a high safety risk.

SUMMARY OF THE INVENTION

The embodiments of the invention are defined, respectively, by the independent and dependent claims appended hereto, which for the sake of brevity are incorporated by reference herein. Other embodiments, features, and advantages of the various aspects of the invention are apparent from the detailed description below taken in conjunction with the appended drawing figures.

In certain embodiments, the present invention provides anti-IL-12/IL-23p40 antibodies expressed in Chinese Hamster Ovary cells (CHO cells). The "anti-IL-12/IL-23p40 Antibodies" defined by the invention comprise antibodies having the amino acid sequences selected from the group consisting of: (i) a heavy chain (HC) comprising the amino acid sequence of SEQ ID NO:10 and a light chain (LC) comprising the amino acid sequence of SEQ ID NO:11; (ii) a heavy chain variable domain amino acid sequence of SEQ ID NO: 7 and a light chain variable domain amino acid sequence of SEQ ID NO:8; and (iii) heavy chain CDR amino acid sequences of SEQ ID NO:1, SEQ ID NO:2, and SEQ ID NO: 3, and light chain CDR amino acid sequences of SEQ ID NO:4, SEQ ID NO:5, and SEQ ID NO: 6, expressed in Chinese Hamster Ovary cells (CHO cells).

In certain embodiments, the oligosaccharide profile of the anti-IL-12/IL-23p40 Antibodies comprises total neutral oligosaccharide species>99.0% and total charged oligosaccharide species<1.0%. In other embodiments, (i) the oligosaccharide profile of the anti-IL-12/IL-23p40 Antibodies comprises total neutral oligosaccharide species>99.0%, total charged oligosaccharide species<1.0%, and individual neutral oligosaccharide species G0F>70.0%, G1F<20.0%, and G2F<5.0%; (ii) the oligosaccharide profile comprising total neutral oligosaccharide species>99.0% and total charged oligosaccharide species<1.0% and the peak 3 area % of the capillary isoelectric focusing (cIEF) electropherogram of the anti-IL-12/IL-23p40 Antibodies is >70.0%; (iii) the anti-IL-12/IL-23p40 Antibodies have no disialylated glycan species as determined by High Performance Liquid Chromatography (HPLC) or Reduced Mass Analysis (RMA); (iv) the anti-IL-12/IL-23p40 Antibodies have a longer half-life compared to anti-IL-12/IL-23p40 antibodies expressed in Sp2/0 cells; and/or (v) the anti-IL-12/IL-23p40 antibodies are a follow-on biologic (antibodies relying on the regulatory approval of and/or data generated with ustekinumab) to ustekinumab (marketed by Janssen Biotech, Inc. as Stelara®).

In certain embodiments, the present invention provides a method of manufacture for producing anti-IL-12/IL-23p40 Antibodies comprising: a. culturing Chinese Hamster Ovary cells (CHO cells); b. expressing the anti-IL-12/IL-23p40 antibodies in the CHO cells; and, c. purifying the anti-IL-12/IL-23p40 antibodies, wherein (i) the oligosaccharide profile of the anti-IL-12/IL-23p40 Antibodies comprises total neutral oligosaccharide species>99.0% and total charged oligosaccharide species<1.0%; (ii) the oligosaccharide profile of the anti-IL-12/IL-23p40 Antibodies comprises total neutral oligosaccharide species>99.0%, total charged oligosaccharide species<1.0%, and individual neutral oligosaccharide species G0F>70.0%, G1F<20.0%, and G2F<5.0%; (iii) the oligosaccharide profile comprising total neutral oligosaccharide species>99.0% and total charged oligosaccharide species<1.0% and the peak 3 area % of the capillary isoelectric focusing (cIEF) electropherogram of the anti-IL-12/IL-23p40 Antibodies is >70.0%; (iv) the anti-IL-12/IL-23p40 Antibodies have no disialylated glycan species as determined by High Performance Liquid Chromatography (HPLC) or Reduced Mass Analysis (RMA); (v) the anti-IL-12/IL-23p40 Antibodies have a longer half-life compared to anti-IL-12/IL-23p40 antibodies expressed in Sp2/0 cells; and/or (vi) the anti-IL-12/IL-23p40 antibodies are a follow-on biologic to ustekinumab.

In certain embodiments, the present invention provides a composition comprising anti-IL-12/IL-23p40 Antibodies, wherein (i) the oligosaccharide profile of the anti-IL-12/IL-23p40 Antibodies comprises total neutral oligosaccharide species>99.0% and total charged oligosaccharide species<1.0%; (ii) the oligosaccharide profile of the anti-IL-12/IL-23p40 Antibodies comprises total neutral oligosaccharide species>99.0%, total charged oligosaccharide species<1.0%, and individual neutral oligosaccharide species G0F>70.0%, G1F<20.0%, and G2F<5.0%; (iii) the oligosaccharide profile comprising total neutral oligosaccharide species>99.0% and total charged oligosaccharide species<1.0% and the peak 3 area % of the capillary isoelectric focusing (cIEF) electropherogram of the anti-IL-12/IL-23p40 Antibodies is >70.0%; (iv) the anti-IL-12/IL-23p40 Antibodies have no disialylated glycan species as determined by High Performance Liquid Chromatography (HPLC) or Reduced Mass Analysis (RMA); (v) the anti-IL-12/IL-23p40 Antibodies have a longer half-life compared to anti-IL-12/IL-23p40 antibodies expressed in Sp2/0 cells; and/or (vi) the anti-IL-12/IL-23p40 antibodies are a follow-on biologic to ustekinumab.

DETAILED DESCRIPTION OF THE PREFERRED EMBODIMENTS

Figure 1:
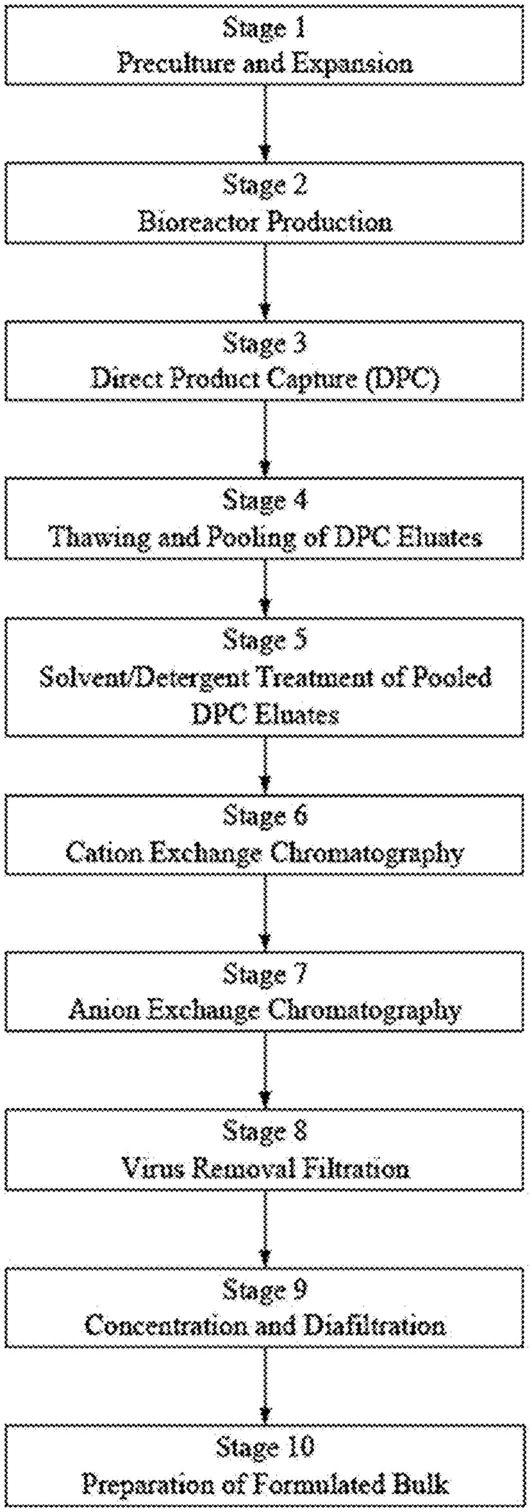
FIG. 1 shows an overview of the 10 stages of the ustekinumab manufacturing process.

As used herein, an "anti-IL-12 antibody," "anti-IL-23 antibody," "anti-IL-12/23p40 antibody," "anti-IL-12/IL-23p40 antibody," "IL-12/23p40 antibody," "IL-12/IL-23p40 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-12 and/or IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-12/23 activity or binding, or with IL-12/23 receptor activity or binding, in vitro, in situ and/or in vivo. As a non-limiting example, a suitable anti-IL-12/23p40 antibody, specified portion or variant of the present invention can bind at least one IL-12/23 molecule, or specified portions, variants or domains thereof. A suitable anti-IL-12/23p40 antibody, specified portion, or variant can also optionally affect at least one of IL-12/23 activity or function, such as but not limited to, RNA, DNA or protein synthesis, IL-12/23 release, IL-12/23 receptor signaling, membrane IL-12/23 cleavage, IL-12/23 activity, IL-12/23 production and/or synthesis.

As used herein, the terms "antibody" or "antibodies", include biosimilar antibody molecules approved under the Biologics Price Competition and Innovation Act of 2009 (BPCI Act) and similar laws and regulations globally. Under the BPCI Act, an antibody may be demonstrated to be biosimilar if data show that it is "highly similar" to the reference product notwithstanding minor differences in clinically inactive components and are "expected" to produce the same clinical result as the reference product in terms of safety, purity and potency (*Endocrine Practice:* February 2018, Vol. 24, No. 2, pp. 195-204). These biosimilar antibody molecules are provided an abbreviated approval pathway, whereby the applicant relies upon the innovator reference product's clinical data to secure regulatory approval. Compared to the original innovator reference antibody that was FDA approved based on successful clinical trials, a biosimilar antibody molecule is referred to herein as a "follow-on biologic". As presented herein, STELARA® (ustekinumab) is the original innovator reference anti-IL-12/23p40 antibody that was FDA approved based on successful clinical trials. Ustekinumab has been on sale in the United States since 2009.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-12/23. For example, antibody fragments capable of binding to IL-12/23 or portions thereof, including, but not limited to, Fab (e.g., by papain digestion), Fab' (e.g., by pepsin digestion and partial reduction) and $F(ab')_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F(ab')_2$ heavy chain portion can be designed to include DNA sequences encoding the $C_H1$ domain and/or hinge region of the heavy chain. The various portions of antibodies can be joined together chemically by conventional techniques or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" may also be an antibody that is derived from or closely matches human germline immunoglobulin sequences. Human antibodies may include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Anti-IL-12/23p40 antibodies (also termed IL-12/23p40 antibodies) (or antibodies to IL-23) useful in the methods and compositions of the present invention can optionally be characterized by high affinity binding to IL-12/23p40 (or to IL-23) and, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., *Lancet* 344: 1125-1127 (1994)), entirely incorporated herein by reference). "Low immunogenicity" can also be defined as the incidence of titrable levels of antibodies to the anti-IL-12 antibody in patients treated with anti-IL-12 antibody as occurring in less than 25% of patients treated, preferably, in less than 10% of patients treated with the recommended dose for the recommended course of therapy during the treatment period.

As used herein, the term "human antibody" refers to an antibody in which substantially every part of the protein (e.g., CDR, framework, $C_L$, $C_H$ domains (e.g., $C_H1$, $C_H2$, and $C_H3$), hinge, ($V_L$, $V_H$)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific (e.g., DuoBody®), heterospecific, heteroconjugate or similar antibodies can also be used that are monoclonal, preferably human or humanized, antibodies that have binding specificities for at least two different antigens. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature* 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, can be cumbersome with low product yields and different strategies have been developed to facilitate bispecific antibody production.

Full length bispecific antibodies can be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent monospecific antibodies are reduced. The resulting free cysteines of one of the parent monospecific antibodies form an inter heavy-chain disulfide bond with cysteine residues of a second parent monospecific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each can bind a distinct epitope.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Intl. Publ. No. WO 2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by following substitutions (expressed as modified position in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/

T350V_T366L_K392L_T394W as described in U.S. Pat. Publ. No. US2012/0149876 or U.S. Pat. Publ. No. US2013/0195849.

In addition to methods described above, bispecific antibodies can be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody and the second monospecific bivalent antibody are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptocthylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptocthylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

The terms "efficacy" and "effective" as used herein in the context of a dose, dosage regimen, treatment or method refer to the effectiveness of a particular dose, dosage or treatment regimen. Efficacy can be measured based on change in the course of the disease in response to an agent of the present invention. For example, an anti-IL12/23p40 or anti-IL23 antibody of the present invention (e.g., the anti-IL12/23p40 antibody usetkinumab) is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease.

The term "safe", as it relates to a dose, dosage regimen, treatment or method with an anti-IL12/23p40 or anti-IL23 antibody of the present invention (e.g., the anti-IL12/23p40 antibody ustekinumab), refers to a favorable risk: benefit ratio with an acceptable frequency and/or acceptable severity of treatment-emergent adverse events (referred to as AEs or TEAEs) compared to the standard of care or to another comparator. An adverse event is an untoward medical occurrence in a patient administered a medicinal product. In particular, safe as it relates to a dose, dosage regimen or treatment with an anti-IL12/23p40 or anti-IL23 antibody of the present invention refers to with an acceptable frequency and/or acceptable severity of adverse events associated with administration of the antibody if attribution is considered to be possible, probable, or very likely due to the use of the anti-IL12/23p40 or anti-IL23 antibody.

Utility

The isolated nucleic acids of the present invention can be used for production of at least one anti-IL-12/23p40 (or anti-IL-23) antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one IL-12/23 condition, selected from, but not limited to, at least one of an immune disorder or disease, a cardiovascular disorder or disease, an infectious, malignant, and/or neurologic disorder or disease, or other known or specified IL-12/23 related condition.

Such a method can comprise administering an effective amount of a composition or a pharmaceutical composition comprising at least one anti-IL-12/23p40 (or anti-IL-23) antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

Citations

All publications or patents cited herein, whether or not specifically designated, are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, NY (1987-2001); Sambrook, et al., Molecular Cloning: A Laboratory Manual, 2nd Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

Antibodies of the Present Invention—Production and Generation

At least one anti-IL-12/23p40 (or anti-IL-23) used in the method of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001), each entirely incorporated herein by reference.

A preferred anti-IL-12/23p40 antibody is ustekinumab (STELARA®) having the heavy chain variable region amino acid sequence of SEQ ID NO:7 and the light chain variable region amino acid sequence of SEQ ID NO:8 and having the heavy chain CDR amino acid sequences of SEQ ID NO:1, SEQ ID NO:2, and SEQ ID NO: 3; and the light chain CDR amino acid sequences of SEQ ID NO:4, SEQ ID NO:5, and SEQ ID NO:6. A preferred anti-IL-23 antibody is guselkumab (also referred to as CNTO1959). Other anti-IL-23 antibodies have sequences listed herein and are described in U.S. Pat. No. 7,935,344, the entire contents of which are incorporated herein by reference).

Human antibodies that are specific for human IL-12/23p40 or IL-23 proteins or fragments thereof can be raised against an appropriate immunogenic antigen, such as an isolated IL-12/23p40 protein, IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, CA; Ixsys. Sec, e.g., EP 368,684, PCT/GB91/01134; PCT/GB92/01755; PCT/GB92/002240; PCT/GB92/00883; PCT/GB93/00605; U.S. Ser. No. 08/350260(May 12, 94); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, MA; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or another mammal. These non-human amino acid residues are replaced by residues often referred to as "import" residues, which are typically taken from an "import" variable, constant or other domain of a known human sequence.

Known human Ig sequences are disclosed, e.g.,
www.ncbi.nlm.nih.gov/entrez/query.fcgi;
www.ncbi.nih.gov/igblast;
www.atcc.org/phage/hdb.html;
www.mrc-cpe.cam.ac.uk/ALIGNMENTS.php;
www.kabatdatabase.com/top.html; ftp.ncbi.nih.gov/repository/kabat;
www.sciquest.com;
www.abcam.com;
www.antibodyresource.com/onlinecomp.html;
www.public.iastate.edu/~pedro/research_tools.html;
www.whfreeman.com/immunology/CH05/kuby05.htm;
www.hhmi.org/grants/lectures/1996/vlab;
www.path.cam.ac.uk/~mrc7/mikeimages.html;
www.mcb.harvard.edu/BioLinks/Immunology.html;

www.immunologylink.com; pathbox.wustl.edu/~hcenter/index.html;
www.appliedbiosystems.com;
www.nal.usda.gov/awic/pubs/antibody;
www.m.ehime-u.ac.jp/~yasuhito/Elisa.html;
www.biodesign.com;
www.cancerresearchuk.org;
www.biotech.ufl.edu;
www.isac-net.org; baserv.uci.kun.nl/~jraats/links1.html;
www.recab.uni-hd.de/immuno.bme.nwu.edu;
www.mrc-cpe.cam.ac.uk;
www.ibt.unam.mx/vir/V_mice.html; http://www.bioinf.org.uk/abs; antibody.bath.ac.uk;
www.unizh.ch;
www.cryst.bbk.ac.uk/~ubcg07s;
www.nimr.mrc.ac.uk/CC/ccaewg/ccaewg.html;
www.path.cam.ac.uk/~mrc7/humanisation/TAHHP.html;
www.ibt.unam.mx/vir/structure/stat_aim.html;
www.biosci.missouri.edu/smithgp/index.html;
www.jerini.de;
Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human anti-IL-12/23p40 (or anti-IL-23) specific antibody used in the method of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human anti-IL-12/23p40 (or anti-IL-23) specific antibody used in the method of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151:2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively, or additionally, it may be useful to combine amino acid modifications with one or more further amino acid modifications that alter C1q binding and/or the complement dependent cytotoxicity function of the Fc region of an IL-23 binding molecule. The starting polypeptide of particular interest may be one that binds to C1q and displays complement dependent cytotoxicity (CDC). Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human anti-IL-12/23p40 (or anti-IL-23) specific antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human anti-IL-12/23p40 (or anti-IL-23) antibody with improved C1q binding and improved FcγRIIIbinding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., 2001). High resolution mapping of the binding site on human IgG1 for FcγRI, FcγRII, FcγRIII, and FcRn and design of IgG1 variants with improved binding to the FcγR, (J. Biol. Chem. 276:6591-6604).

Another type of amino acid substitution serves to alter the glycosylation pattern of the Fc region of the human anti-IL-12/23p40 (or anti-IL-23) specific antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation sites that are not present in the polypeptide. Addition of glycosylation sites to the Fc region of a human IL-23 specific antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human anti-IL-12/23p40 (or anti-IL-23) specific antibody of the present invention is expressed in cells that express beta (1,4)-N-acetylglucosaminyltransferase III (GnT III), such that GnT III adds GlcNAc to the human anti-IL-12/23p40 (or anti-IL-23) antibody. Methods for producing antibodies in such a fashion are provided in WO/9954342, WO/03011878, patent publication 20030003097A1, and Umana et al., Nature Biotechnology, 17:176-180, February 1999; all of which are herein specifically incorporated by reference in their entireties.

The human anti-IL-12/23p40 (or anti-IL-23) antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-12/23p40 (or anti-IL-23) antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6 (4) 579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, CA), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge antibody Technologies; U.S. Pat. No. 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL-12/23p40 (or anti-IL-23) antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies used in the method of the present invention can additionally be prepared using at least one anti-IL-12/23p40 (or anti-IL-23) antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies used in the method of the invention can bind human IL-12/IL-23p40 or IL-23 with a wide range of affinities ($K_D$). In a preferred embodiment, a human mAb can optionally bind human IL-12/IL-23p40 or IL-23 with high affinity. For example, a human mAb can bind human IL-12/IL-23p40 or IL-23 with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology,* Paul, W. E., Ed., Raven Press: New York, NY (1984); Kuby, Janis *Immunology,* W. H. Freeman and Company: New York, NY (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, for example, the nucleotide sequences encoding at least 70-100% of the contiguous amino acids of at least one of the light or heavy chain variable or CDR regions described herein, among other sequences disclosed herein, specified fragments, variants or consensus sequences thereof, or a deposited vector comprising at least one of these sequences, a nucleic acid molecule of the present invention encoding at least one IL-12/IL-23p40 or IL-23 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules used in the method of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain or light chain; nucleic acid molecules comprising the coding sequence for an anti-IL-12/IL-23p40 or IL-23 antibody or variable region; and nucleic acid molecules which comprise a nucleotide sequence substantially different from those described above but which, due to the degeneracy of the genetic code, still encode at least one anti-IL-12/IL-23p40 or IL-23 antibody as described herein and/or as known in the art. Of course, the genetic code is well known in the art. Thus, it would be routine for one skilled in the art to generate such degenerate nucleic acid variants that code for specific anti-IL-12/IL-23p40 or IL-23 antibodies used in the method of the present invention. See, e.g., Ausubel, et al., supra, and such nucleic acid variants are included in the present invention. Non-limiting examples of isolated nucleic acid molecules include nucleic acids encoding HC CDR1, HC CDR2, HC CDR3, LC CDR1, LC CDR2, and LC CDR3, respectively.

As indicated herein, nucleic acid molecules which comprise a nucleic acid encoding an anti-IL-12/IL-23p40 or IL-23 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The method of the present invention uses isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic, or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of an antibody. The polynucleotides embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide used in the method of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay;

and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides used in the method of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, CA (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids used in the method of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-23 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS) (U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be affected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Cells useful for the production of the antibodies, specified portions or variants thereof, include mammalian cells. Mammalian cell systems often will be cultured in the form of monolayers of cells, but the cells can also be adapted to grow in suspension, e.g., in shake flasks or bioreactors. A number of suitable host cell lines capable of expressing intact glycosylated proteins have been developed in the art, and include, e.g., COS-1 (e.g., ATCC® CRL1650), COS-7 (e.g., ATCC® CRL-1651), HEK293, BHK21 (e.g., ATCC® CCL-10), BSC-1 (e.g., ATCC® CCL-26), Chinese hamster ovary (CHO), Hep G2, P3X63Ag8.653, Sp2/0-Ag14, HeLa and the like, which are readily available from, for example, American Type Culture Collection, Manassas, Va (www.atcc.org). In certain embodiments, host cells include CHO cells and cells of lymphoid origin, such as myeloma and lymphoma cells, e.g., CHO-K1 cells, P3X63Ag8.653 cells (ATCC® CRL-1580) and Sp2/0-Ag14 cells (ATCC® CRL-1581).

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

CHO Cell Lines

Despite the availability of several other mammalian cell lines, a majority of recombinant therapeutic proteins produced today are made in Chinese hamster ovary (CHO) cells (Jayapal KP, et al. Recombinant protein therapeutics from CHO cells-20 years and counting. *Chem Eng Prog.* 2007; 103:40-47; Kunert R, Reinhart D. Advances in recombinant antibody manufacturing. *Appl Microbiol Biotechnol.* 2016; 100(8):3451-61). Their strengths include, e.g., robust growth as adherent cells or in suspension, adaptability to serum-free and chemically defined media, high productivity, and an established history of regulatory approval for therapeutic recombinant protein production. They are also very amenable to genetic modifications and the methods for cell transfection, recombinant protein expression, and clone selection are all well characterized. CHO cells can also provide human-compatible post-translational modifications. As used herein, "CHO cells" include, but are not limited to, e.g., CHO-DG44, CHO-Kl, CHO-M, CHO-S, CHO GS knockout, and modifications and derivatives thereof.

Cloning and Expression in CHO Cells

One vector commonly used for expression in CHO cells is pC4. Plasmid pC4 is a derivative of the plasmid pSV2-dhfr (ATCC® 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (e.g., alpha minus MEM, Life Technologies, Gaithersburg, MD) supplemented with the chemotherapeutic agent methotrexate. The amplification of the DHFR genes in cells resistant to methotrexate (MTX) has been well documented (see, e.g., F. W. Alt, et al., *J. Biol. Chem.* 253:1357-1370 (1978); J. L. Hamlin and C. Ma, *Biochem. et Biophys. Acta* 1097:107-143 (1990); and M. J. Page and M. A. Sydenham, *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molec. Cell. Biol.* 5:438-447 (1985)) plus a fragment isolated from the enhancer of the immediate early gene of human cytomegalovirus (CMV) (Boshart, et al., *Cell* 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human beta-actin promoter, the SV40 early or late promoters or the long terminal repeats from other retroviruses, e.g., HIV and HTLVI. Clontech's Tet-Off and Tet-On gene expression systems and similar systems can also be used to express proteins in a regulated way in mammalian cells (M. Gossen, and H. Bujard, *Proc. Natl. Acad. Sci. USA* 89:5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

Purification of an Antibody

An anti-IL-12/IL-23p40 or IL-23 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, NY, (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-12/IL-23p40 or IL-23 Antibodies

An anti-IL-12/IL-23p40 or IL-23 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one $C_H1$, hinge1, hinge2, hinge3, hinge4, $C_H2$, or $C_H3$ or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

The isolated antibodies used in the method of the present invention comprise the antibody amino acid sequences disclosed herein encoded by any suitable polynucleotide, or any isolated or prepared antibody. Preferably, the human antibody or antigen-binding fragment binds human IL-12/IL-23p40 or IL-23 and, thereby, partially or substantially neutralizes at least one biological activity of the protein. An antibody, or specified portion or variant thereof, that partially or preferably substantially neutralizes at least one biological activity of at least one IL-12/IL-23p40 or IL-23 protein or fragment can bind the protein or fragment and thereby inhibit activities mediated through the binding of IL-12/IL-23p40 or IL-23 to the IL-12 and/or IL-23 receptor or through other IL-12/IL-23p40 or IL-23-dependent or mediated mechanisms. As used herein, the term “neutralizing antibody” refers to an antibody that can inhibit an IL-12/IL-23p40 or IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-12/IL-23p40 or IL-23 antibody to inhibit an IL-12/IL-23p40 or IL-23-dependent activity is preferably assessed by at least one suitable IL-12/IL-23p40 or IL-23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other trangenic non-human mammal comprising at least one human light chain (e.g., IgG, IgA, and IgM) transgenes as described herein and/or as known in the art. In another embodiment, the anti-IL-23 human antibody comprises an IgG1 heavy chain and an IgG1 light chain.

An antibody binds at least one specified epitope specific to at least one IL-12/IL-23p40 or IL-23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original non-human CDRs can be used. These CDRs may be formed by incorporation of conservative substitutions from the original non-human sequence. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-12/IL-23p40 or IL-23 specific antibody can comprise at least one of a heavy or light chain variable region having a defined amino acid sequence. For example, in a preferred embodiment, the anti-IL-12/IL-23p40 or IL-23 antibody comprises an anti-IL-12/IL-23p40 antibody with a heavy chain variable region comprising the amino acid sequence of SEQ ID NO:7 and a light chain variable region comprising the amino acid sequence of SEQ ID NO:8. The anti-IL-12/IL-23p40 or IL-23 specific antibody can also comprise at least one of a heavy or light chain having a defined amino acid sequence. In another preferred embodiment, the anti-IL-12/IL-23p40 or IL-23 antibody comprises an anti-IL-12/IL-23p40 antibody with a heavy chain comprising the amino acid sequence of SEQ ID NO:10 and a light chain comprising the amino acid sequence of SEQ ID NO:11. Antibodies that bind to human IL-12/IL-23p40 or IL-23 and that comprise a defined heavy or light chain variable region can be prepared using suitable methods, such as phage display (Katsube, Y., et al., *Int J Mol. Med,* 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-12/IL-23p40 or IL-23 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-12/IL-23p40 or IL-23 with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include, without limitation, replacement of one amino acid by another within the following groups: lysine (K), arginine (R) and histidine (H); aspartate (D) and glutamate (E); asparagine (N), glutamine (Q), serine(S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-IL-12/IL-23p40 or IL-23 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

Sequences

Example Anti-IL-12/IL-23p40 Antibody Sequences—STELARA® (ustekinumab)

Amino acid sequence of anti-IL-12/IL-23p40 antibody complementarity determining region heavy chain 1 (CDRH1):

(SEQ ID NO: 1)

TYWLG

Amino acid sequence of anti-IL-12/IL-23p40 antibody complementarity determining region heavy chain 2 (CDRH2):

(SEQ ID NO: 2)

IMSPVDSDIRYSPSFQG

Amino acid sequence of anti-IL-12/IL-23p40 antibody complementarity determining region heavy chain 3 (CDRH3):

(SEQ ID NO: 3)

RRPGQGYFDF

Amino acid sequence of anti-IL-12/IL-23p40 antibody complementarity determining region light chain 1 (CDRL1):

(SEQ ID NO: 4)

RASQGISSWLA

Amino acid sequence of anti-IL-12/IL-23p40 antibody complementarity determining region light chain 2 (CDRL2):

(SEQ ID NO: 5)

AASSLQS

Amino acid sequence of anti-IL-12/IL-23p40 antibody complementarity determining region light chain 3 (CDRL3):

(SEQ ID NO: 6)

QQYNIYPYT

Amino acid sequence of anti-IL-12/IL-23p40 antibody variable heavy chain region (CDRs underlined):

(SEQ ID NO: 7)

-continued

```
1    EVQLVQSGAE VKKPGESLKI SCKGSGYSFT TYWLGWVRQM PGKGLDWIGI MSPVDSDIRY

61   SPSFQGQVTM SVDKSITTAY LQWNSLKASD TAMYYCARRR PGQGYFDFWG QGTLVTVSS
```

Amino acid sequence of anti-IL-12/IL-23p40 antibody variable light chain region (CDRs underlined):

(SEQ ID NO: 8)

```
1    DIQMTQSPSS LSASVGDRVT ITCRASQGIS SWLAWYQQKP EKAPKSLIYA ASSLQSGVPS

61   RFSGSGSGTD FTLTISSLQP EDFATYYCQQ YNIYPYTFGQ GTKLEIKR
```

Amino acid sequence of anti-IL-12/IL-23p40 antibody heavy chain (CDRs underlined):

(SEQ ID NO: 10)

```
1    EVQLVQSGAE VKKPGESLKI SCKGSGYSFT TYWLGWVRQM PGKGLDWIGI MSPVDSDIRY

61   SPSFQGQVTM SVDKSITTAY LQWNSLKASD TAMYYCARRR PGQGYFDFWG QGTLVTVSSS

121  STKGPSVFPL APSSKSTSGG TAALGCLVKD YFPEPVTVSW NSGALTSGVH TFPAVLQSSG

181  LYSLSSVVTV PSSSLGTQTY ICNVNHKPSN TKVDKRVEPK SCDKTHTCPP CPAPELLGGP

241  SVFLFPPKPK DTLMISRTPE VTCVVVDVSH EDPEVKFNWY VDGVEVHNAK TKPREEQYNS

301  TYRVVSVLTV LHQDWLNGKE YKCKVSNKAL PAPIEKTISK AKGQPREPQV YTLPPSRDEL

361  TKNQVSLTCL VKGFYPSDIA VEWESNGQPE NNYKTTPPVL DSDGSFFLYS KLTVDKSRWQ

421  QGNVFSCSVM HEALHNHYTQ KSLSLSPGK
```

Amino acid sequence of anti-IL-12/IL-23p40 antibody light chain (CDRs underlined):

(SEQ ID NO: 11)

```
1    DIQMTQSPSS LSASVGDRVT ITCRASQGIS SWLAWYQQKP EKAPKSLIYA ASSLQSGVPS

61   RFSGSGSGTD FTLTISSLQP EDFATYYCQQ YNIYPYTFGQ GTKLEIKRTV AAPSVFIFPP

121  SDEQLKSGTA SVVCLLNNFY PREAKVQWKV DNALQSGNSQ ESVTEQDSKD STYSLSSTLT

181  LSKADYEKHK VYACEVTHQG LSSPVTKSFN RGEC
```

Amino Acid Sequence IL-12

Amino acid sequence of human interleukin (IL)-12 with alpha and beta subunits:

(SEQ ID NO: 9)

```
1    RNLPVATPDP GMFPCLHHSQ NLLRAVSNML QKARQTLEFY PCTSEEIDHE DITKDKTSTV

61   EACLPLELTK NESCLNSRET SFITNGSCLA SRKTSFMMAL CLSSIYEDLK MYQVEFKTMN

121  AKLLMDPKRQ IFLDQNMLAV IDELMQALNF NSETVPQKSS LEEPDFYKTK IKLCILLHAF

181  RIRAVTIDRV MSYLNASIWE LKKDVYVVEL DWYPDAPGEM VVLTCDTPEE DGITWTLDQS

241  SEVLGSGKTL TIQVKEFGDA GQYTCHKGGE VLSHSLLLLH KKEDGIWSTD ILKDQKEPKN

301  KTFLRCEAKN YSGRFTCWWL TTISTDLTFS VKSSRGSSDP QGVTCGAATL SAERVRGDNK

361  EYEYSVECQE DSACPAAEES LPIEVMVDAV HKLKYENYTS SFFIRDIIKP DPPKNLQLKP

421  LKNSRQVEVS WEYPDTWSTP HSYFSLTFCV QVQGKSKREK KDRVFTDKTS ATVICRKNAS

481  ISVRAQDRYY SSSWSEWASV PCS
```

An anti-IL-12/IL-23p40 or IL-23 antibody used in the method of the present invention can include one or more amino acid substitutions, deletions or additions, either from natural mutations or human manipulation, as specified herein.

The number of amino acid substitutions a skilled artisan would make depends on many factors, including those described above. Generally speaking, the number of amino acid substitutions, insertions or deletions for any given anti-IL-12/IL-23p40 or IL-23 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-IL-12/IL-23p40 or IL-23 specific antibody that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-12/IL-23p40 or IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)).

Anti-IL-12/IL-23p40 or IL-23 antibodies can include, but are not limited to, at least one portion, sequence or combination selected from 5 to all of the contiguous amino acids of at least one of SEQ ID NOs 1, 2, 3, 4, 5, 6, 7, 8, 10, or 11.

IL-12/IL-23p40 or IL-23 antibodies or specified portions or variants can include, but are not limited to, at least one portion, sequence or combination selected from at least 3-5 contiguous amino acids of the SEQ ID NOs above; 5-17 contiguous amino acids of the SEQ ID NOs above, 5-10 contiguous amino acids of the SEQ ID NOs above, 5-11 contiguous amino acids of the SEQ ID NOs above, 5-7 contiguous amino acids of the SEQ ID NOS above; 5-9 contiguous amino acids of the SEQ ID NOs above.

An anti-IL-12/IL-23p40 or IL-23 antibody can further optionally comprise a polypeptide of at least one of 70-100% of 5, 17, 10, 11, 7, 9, 119, 108, 449, or 214 contiguous amino acids of the SEQ ID NOs above. In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of the SEQ ID NOs above. For example, the amino acid sequence of a light chain variable region can be compared with the sequence of the SEQ ID NOs above, or the amino acid sequence of a heavy chain CDR3 can be compared with the SEQ ID NOs above. Preferably, 70-100% amino acid identity (i.e., 90, 91, 92, 93, 94, 95, 96, 97, 98, 99, 100 or any range or value therein) is determined using a suitable computer algorithm, as known in the art.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, MD).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

Preferred parameters for polypeptide sequence comparison include the following:

(1) Algorithm: Needleman and Wunsch, J. Mol Biol. 48:443-453 (1970) Comparison matrix: BLOSSUM62 from Hentikoff and Hentikoff, Proc. Natl. Acad. Sci, USA. 89:10915-10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:

(1) Algorithm: Needleman and Wunsch, J. Mol Biol. 48:443-453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid sequence comparisons.

By way of example, a polynucleotide sequence may be identical to another sequence, that is 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or:

n.sub.n.ltorsim.x.sub.n−(x.sub.n.y), wherein n.sub.n is the number of nucleotide alterations, x.sub.n is the total number of nucleotides in sequence, and y is, for instance, 0.70 for 70%, 0.80 for 80%, 0.85 for 85%, 0.90 for 90%, 0.95 for 95%, etc., and wherein any non-integer product of x.sub.n and y is rounded down to the nearest integer prior to subtracting from x.sub.n.

Alterations of a polynucleotide sequence encoding the the SEQ ID NOs above may create nonsense, missense or frameshift mutations in this coding sequence and thereby alter the polypeptide encoded by the polynucleotide following such alterations. Similarly, a polypeptide sequence may be identical to the reference sequence of the SEQ ID NOs above, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the SEQ ID NOs above by the numerical percent of the respective percent identity (divided by 100) and then subtracting that product from the total number of amino acids in the SEQ ID NOs above, or: n.sub.a.ltorsim.x.sub.a−(x.sub.a.y), wherein n.sub.a is the number of amino acid alterations, x.sub.a is the total number of amino acids in the SEQ ID NOs above, and y is, for instance 0.70 for 70%, 0.80 for 80%, 0.85 for 85% etc., and wherein any non-integer produce of x.sub.a and y is rounded down to the nearest integer prior to subtracting it from x.sub.a.

Exemplary heavy chain and light chain variable regions sequences and portions thereof are provided in the SEQ ID NOs above. The antibodies of the present invention, or specified variants thereof, can comprise any number of contiguous amino acid residues from an antibody of the present invention, wherein that number is selected from the group of integers consisting of from 10-100% of the number of contiguous residues in an anti-IL-12/IL-23p40 or IL-23 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% or more (including, without limitation, up to 10 times the specific activity) of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

As defined herein, the term "half-life" indicates that the plasma concentration of a drug (e.g., a therapeutic anti-IL-12/IL-23p40 antibody ustekinumab) is halved after one elimination half-life. Therefore, in each succeeding half-life, less drug is eliminated. After one half-life the amount of drug remaining in the body is 50% after two half-lives 25%, etc. The half-life of a drug depends on its clearance and volume of distribution. The elimination half-life is considered to be independent of the amount of drug in the body.

The modified antibodies and antigen-binding fragments can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques,* Academic Press: San Diego, CA (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.,* 3:147-153 (1992); Werlen et al., *Bioconjugate Chem.,* 5:411-417 (1994); Kumaran et al., *Protein Sci.* 6(10):2233-2241 (1997); Itoh et al., *Bioorg. Chem.,* 24(1): 59-68 (1996); Capellas et al., *Biotechnol. Bioeng.,* 56(4):456-463 (1997)), and the methods described in Hermanson, G. T., *Bioconjugate Techniques,* Academic Press: San Diego, CA (1996).

The method of the present invention also uses an anti-IL-12/IL-23p40 or IL-23 antibody composition comprising at least one, at least two, at least three, at least four, at least five, at least six or more anti-IL-12/IL-23p40 or IL-23 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-12/IL-23p40 or IL-23 antibody amino acid sequence selected from the group consisting of 70-100% of the contiguous amino acids of the SEQ ID NOs above, or specified fragments, domains or variants thereof. Preferred anti-IL-12/IL-23p40 or IL-23 antibody compositions include at least one or two full length, fragments, domains or variants as at least one CDR or LBP containing portions of the anti-IL-12/IL-23p40 or IL-23 antibody sequence described herein, for example, 70-100% of the SEQ ID NOs above, or specified fragments, domains or variants thereof. Further preferred compositions comprise, for example, 40-99% of at least one of 70-100% of the SEQ ID NOS above, etc., or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antincoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, $21^{st}$ edition, Springhouse Corp., Springhouse, PA, 2001; Health Professional's Drug Guide 2001, ed., Shannon, Wilson, Stang, Prentice-Hall, Inc, Upper Saddle River, NJ; Pharmcotherapy Handbook, Wells et al., ed., Appleton & Lange, Stamford, CT, each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate.

The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, 6-mercaptopurine, methotrexate, mizoribine, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of *Nursing* 2001 *Drug Handbook*.)

Anti-IL-12/IL-23p40 or IL-23 antibody compositions can further comprise at least one of any suitable and effective amount of a composition or pharmaceutical composition comprising at least one anti-IL-12/IL-23p40 or IL-23 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., basiliximab, cyclosporine, daclizumab), a cytokine or a cytokine antagonist. Non-limiting examples of such cytokines include, but are not limited to, any of IL-1 to IL-23 et al. (e.g., IL-1, IL-2, etc.). Suitable dosages are well known in the art. See, e.g., Wells et al., eds., Pharmacotherapy Handbook, $2^{nd}$ Edition, Appleton and Lange, Stamford, CT (2000); PDR Pharmacopocia, Tarascon Pocket Pharmacopoeia 2000, Deluxe Edition, Tarascon Publishing, Loma Linda, CA (2000), each of which references are entirely incorporated herein by reference.

Anti-IL-12/IL-23p40 or IL-23 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* $18^{th}$ Edition, Mack Publishing Co. (Easton, PA) 1990. Pharmaceutically acceptable carriers can be routinely selected that are suitable for the mode of administration, solubility and/or stability of the anti-IL-23 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-12/IL-23p40 or IL-23 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-12/IL-23p40 or IL-23 antibody compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-12/IL-23p40 or IL-23 antibody, portion or variant compositions according to the invention are known in the art, e.g., as listed in "Remington: The Science & Practice of Pharmacy," $19^{th}$ ed., Williams & Williams, (1995), and in the "Physician's Desk Reference," $52^{nd}$ ed., Medical Economics, Montvale, NJ (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-12/IL-23p40 or IL-23 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-12/IL-23p40 or IL-23 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-12/IL-23p40 or IL-23 antibody, and a second vial comprising an aqueous diluent of prescribed buffer or preservative, wherein said packaging material comprises a label that instructs a patient to reconstitute the anti-IL-12/IL-23p40 or IL-23 antibody in the aqueous diluent to form a solution that can be held over a period of twenty-four hours or greater.

The anti-IL-12/IL-23p40 or IL-23 antibody used in accordance with the present invention can be produced by recombinant means, including from mammalian cell or transgenic preparations, or can be purified from other biological sources, as described herein or as known in the art.

The range of the anti-IL-12/IL-23p40 or IL-23 antibody includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-12/IL-23p40 or IL-23 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-12/IL-23p40 or IL-23 specific antibody and preservative in an aqueous diluent is carried out using conventional dissolution and mixing procedures. To prepare a suitable formulation, for example, a measured amount of at least one anti-IL-12/IL-23p40 or IL-23 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to patients as clear solutions or as dual vials comprising a vial of lyophilized anti-IL-12/IL-23p40 or IL-23 specific antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-12/IL-23p40 or IL-23 specific antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-12/IL-23p40 or IL-23 specific antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-12/IL-23p40 or IL-23 specific antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject® Smartject® e.g., as made or developed by Becton Dickensen (Franklin Lakes, NJ, www.bectondickenson.com), Disetronic (Burgdorf, Switzerland, www.disetronic.com; Bioject, Portland, Oregon (www.bioject.com); National Medical Products, Weston Medical (Peterborough, UK, www.weston-medical.com), Medi-Ject Corp (Minneapolis, MN, www.mediject.com), and similary suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors, and needle free IV infusion sets.

The products may include packaging material. The packaging material provides, in addition to the information required by the regulatory agencies, the conditions under which the product can be used. The packaging material of the present invention provides instructions to the patient, as applicable, to reconstitute the at least one anti-IL-12/IL-23p40 or IL-23 antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-12/IL-23p40 or IL-23 antibody and a selected buffer, preferably, a phosphate buffer containing saline or a chosen salt. Mixing the anti-IL-23 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal patient. Such pharmaceutical compositions are prepared using water at "standard state" as the diluent and routine methods well known to those of ordinary skill in the art. For example, buffering components such as histidine and histidine monohydrochloride hydrate, may be provided first followed by the addition of an appropriate, non-final volume of water diluent, sucrose and polysorbate 80 at "standard state." Isolated antibody may then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions may be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions may contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-12/IL-23p40 or IL-23 specific mAbs bind to similar or different epitopes and/or compete with each other. Abs are individually coated on ELISA plates. Competing mAbs are added, followed by the addition of biotinylated hrIL-12 or IL-23. For positive control, the same mAb for coating may be used as the competing mAb ("self-competition"). IL-12/IL-23p40 or IL-23 binding is detected using streptavidin. These results demonstrate whether the mAbs recognize similar or partially overlapping epitopes on IL-12/IL-23p40 or IL-23.

One aspect of the method of the invention administers to a patient a pharmaceutical composition comprising In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

The stable or preserved formulations can be provided to patients as clear solutions or as dual vials comprising a vial of lyophilized at least one anti-IL-23 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23 antibody may result in other than a clear solution of lyophilized powder comprising the antibody. Among non-clear solutions are formulations comprising particulate suspensions, said particulates being a composition containing the anti-IL-23 antibody in a structure of variable dimension and known variously as a microsphere, microparticle, nanoparticle, nanosphere, or liposome.

Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(−) lactide poly(episilon-caprolactone, poly(epsilon-caprolactone-CO-lactic acid), poly(epsilon-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly (episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

An anti-IL-23 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating lupus, in a cell, tissue, organ, animal, or patient, as known in the art or as described herein, using at least one IL-23 antibody of the present invention, e.g., administering or contacting the cell, tissue, organ, animal, or patient with a therapeutic effective amount of IL-12/IL-23p40 or IL-23 specific antibody.

Any method of the present invention can comprise administering an effective amount of a composition or pharmaceutical composition comprising an anti-IL-23 antibody to a cell, tissue, organ, animal or patient in need of such modulation, treatment or therapy. Such a method can optionally further comprise co-administration or combination therapy for treating such diseases or disorders, wherein the administering of said at least one anti-IL-23 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoictin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, 2$^{nd}$ Edition, Appleton and Lange, Stamford, CT (2000); PDR Pharmacopoeia, Tarascon Pocket Pharmacopocia 2000, Deluxe Edition, Tarascon Publishing, Loma Linda, CA (2000); Nursing 2001 Handbook of Drugs, 21st edition, Springhouse Corp., Springhouse, PA, 2001; Health Professional's Drug Guide 2001, ed., Shannon, Wilson, Stang, Prentice-Hall, Inc, Upper Saddle River, NJ, each of which references are entirely incorporated herein by reference.

Therapeutic Treatments

Typically, treatment of lupus is affected by administering an effective amount or dosage of an anti-IL-12/23p40 or anti-IL-23 antibody composition that total, on average, a range from at least about 0.01 to 500 milligrams of an anti-IL-12/23p40 or anti-IL-23 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 μg/ml serum concentration per single or multiple administrations. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions, the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of an anti-IL-23 antibody. While pulmonary administration is used in the following description, other modes of administration can be used according to the present invention with suitable results. IL-12/IL-23p40 or IL-23 antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthtetic mono-or di-or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-12/IL-23p40 or IL-23 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-12/IL-23p40 or IL-23 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

Example: Manufacturing Processes to Produce STELARA® (ustekinumab)

Background

STELARA® (ustekinumab) is a fully human G1 kappa monoclonal antibody that binds with high affinity and specificity to the shared p40 subunit of human interleukin (IL)-12 and IL-23 cytokines. Ustekinumab comprises a heavy chain of the amino acid sequence of SEQ ID NO: 10 and a light chain of the amino acid sequence of SEQ ID NO: 11; a heavy chain variable domain amino acid sequence of SEQ ID NO:7 and a light chain variable domain amino acid sequence of SEQ ID NO:8; the heavy chain CDR amino acid sequences of SEQ ID NO:1, SEQ ID NO:2, and SEQ ID NO:3; and the light chain CDR amino acid sequences of SEQ ID NO:4, SEQ ID NO:5, and SEQ ID NO:6. The binding of ustekinumab to the IL-12/23p40 subunit blocks the binding of IL-12 or IL-23 to the IL-12RB1 receptor on the surface of natural killer and CD4+T cells, inhibiting IL-12-and IL-23-specific intracellular signaling and subsequent activation and cytokine production. Abnormal regulation of IL-12 and IL-23 has been associated with multiple immune-mediated diseases.

To date, ustekinumab has received marketing approval globally, including countries in North America, Europe, South America, and the Asia-Pacific region, for the treatment of adult patients including those with chronic moderate to severe plaque psoriasis and/or active psoriatic arthritis, Crohn's disease (CD) and ulcerative colitis (UC). Ustekinumab is also being evaluated in a Phase 3 study for the treatment of active Systemic Lupus Erythematosus (SLE).

Manufacturing Process Overview

STELARA® (ustekinumab) is manufactured in a 10-stage process that includes continuous perfusion cell culture followed by purification. An overview of the manufacturing process is provided in FIG. 1.

As used herein, the terms "culture", "culturing", "cultured", and "cell culture" refer to a cell population that is suspended in a medium under conditions suitable to survival and/or growth of the cell population. As will be clear from context to those of ordinary skill in the art, these terms as used herein also refer to the combination comprising the cell population and the medium in which the population is suspended. Cell culture includes, e.g., cells grown by batch, fed-batch or perfusion cell culture methods and the like. In certain embodiments, the cell culture is a mammalian cell culture.

Cell lines for use in the present invention include mammalian cell lines including, but not limited to, Chinese Hamster Ovary cells (CHO cells), human embryonic kidney cells (HEK cells), baby hamster kidney cells (BHK cells), mouse myeloma cells (e.g., NSO cells and Sp2/0 cells), and human retinal cells (e.g., PER.C6 cells).

As used herein, the terms "chemically defined medium", "chemically defined media", "chemically defined hybridoma medium", or "chemically defined hybridoma media" refer to a synthetic growth medium in which the identity and concentration of all the components are known. Chemically defined media do not contain bacterial, yeast, animal, or plant extracts, animal serum or plasma although they may or may not include individual plant or animal-derived components (e.g., proteins, polypeptides, etc). Chemically defined media may contain inorganic salts such as phosphates, sulfates, and the like needed to support growth. The carbon source is defined, and is usually a sugar such as glucose, lactose, galactose, and the like, or other compounds such as glycerol, lactate, acetate, and the like. While certain chemically defined media also use phosphate salts as a buffer, other buffers may be employed such as citrate, triethanolamine, and the like. Examples of commercially available chemically defined media include, but are not limited to, ThermoFisher's CD Hybridoma Medium and CD Hybridoma AGT™ Medium, various Dulbecco's Modified Eagle's (DME) mediums (Sigma-Aldrich Co; SAFC Biosciences, Inc), Ham's Nutrient Mixture (Sigma-Aldrich Co; SAFC Biosciences, Inc), combinations thereof, and the like. Methods of preparing chemically defined mediums are known in the art, for example in U.S. Pat. Nos. 6,171,825 and 6,936,441, WO 2007/077217, and U.S. Patent Application Publication Nos. 2008/0009040 and 2007/0212770.

The term "bioreactor" as used herein refers to any vessel useful for the growth of a cell culture. The bioreactor can be of any size so long as it is useful for the culturing of cells. In certain embodiments, such cells are mammalian cells. Typically, the bioreactor will be at least 1 liter and may be 10, 100, 250, 500, 1,000, 2,500, 5,000, 8,000, 10,000, 12,000 liters or more, or any volume in between. The internal conditions of the bioreactor, including, but not limited to pH and temperature, are optionally controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or glycoprotein of interest. The volume of the production bioreactor is typically at least 500 liters and may be 1,000, 2,500, 5,000, 8,000, 10,000, 12,000 liters or more, or any volume in between. One of ordinary skill in the art will be aware of and will be able to choose suitable bioreactors for use in practicing the present invention.

Preculture, expansion, and production of ustekinumab are performed in Stage 1 and Stage 2. In Stage 1, preculture is initiated from one or more working cell bank vials of transfected Sp2/0 cells expressing the HC and LC sequences of ustekinumab and expanded in culture flasks, disposable culture bags, and a 100 L seed bioreactor. The cells are cultured until the cell density and volume required for inoculation of a 500 L production bioreactor are obtained. In Stage 2, the cell culture is perfused in a 500 L production bioreactor using an alternating tangential flow (ATF) hollow fiber filter cell retention system. Cell culture permeate (harvest) is collected from the ATF system while cells are retained within the bioreactor and the culture is replenished with fresh medium. Harvest from one or more 500L production bioreactors may be combined in Stage 3. The harvests are purified using MabSelect Protein A resin affinity chromatography. The resultant direct product capture (DPC) eluate is frozen until further processing.

Purification of ustekinumab from DPC is performed in Stage 4 through Stage 8 by ion exchange chromatography steps and other steps to inactivate or remove potential virus contamination (solvent/detergent [S/D] treatment and virus removal filtration). DPC eluates are thawed, pooled and filtered in Stage 4 and incubated with Tri-n-butyl Phosphate (TNBP) and polysorbate 80 S/D treatment in Stage 5 to inactivate any lipid-enveloped viruses present. TNBP and polysorbate 80 reagents, aggregates, and impurities are removed from ustekinumab in Stage 6, using SPXL® sepharose cation exchange resin chromatography. Ustekinumab is further purified using QXL® sepharose anion exchange resin chromatography in Stage 7 to remove DNA, viruses, and impurities. In Stage 8, the purified ustekinumab is diluted and filtered through a virus retentive filter (NFP®).

Preparation of the ustekinumab pre-formulated bulk (PFB) and formulated bulk (FB) is performed in Stages 9 and 10, respectively. In Stage 9, the ultrafiltration step concentrates the ustekinumab and the diafiltration step adds the formulation excipients and removes the in-process buffer salts. Polysorbate 80 is added to the ustekinumab PFB in Stage 10 to obtain the FB. The FB is filtered into polycarbonate containers for frozen storage. The frozen FB is packaged in insulated containers with dry ice for transport to the drug product manufacturing site.

Detailed Description of Cell Culture in Large-Scale Manufacturing Process

Stage 1

Preculture and Expansion

Figure 2:
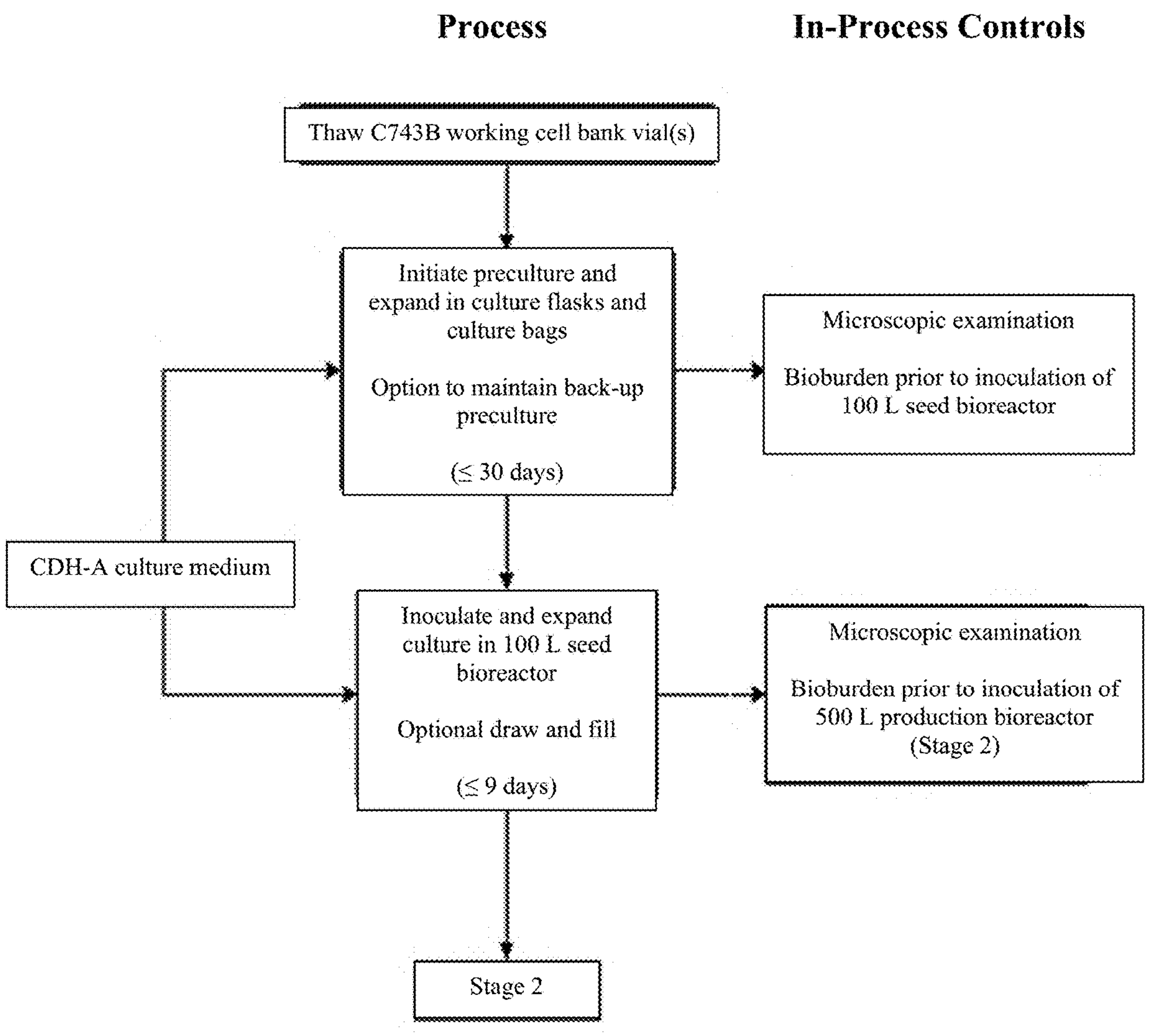
FIG. 2 shows a flow diagram of Stage 1 manufacturing process for the preculture and expansion steps, including the in-process controls and process monitoring tests.

The first stage in the production of ustekinumab is the initiation of preculture from a Working Cell Bank (WCB) vial of transfected Sp2/0 cells expressing the HC and LC sequences of ustekinumab and expanded in culture flasks, disposable culture bags, and a 100L seed bioreactor. The cells are cultured until the cell density and volume required for inoculation of a 500 L production bioreactor are obtained. A flow diagram depicting the preculture and expansion process is provided in FIG. 2.

Manufacturing Procedure

One or more cryopreserved vials of WCB are thawed and diluted with CD (chemically defined) hybridoma medium supplemented with 6 mM L-glutamine, 0.5 mg/L mycophenolic acid, 2.5 mg/L hypoxanthine, and 50 mg/L xanthine (CDH-A). The culture viability must be ≥45%. The cells are further diluted with CDH-A in a culture flask to a seeding density of 0.2 to $0.5\times10^6$ viable cells (VC)/mL. The preculture is maintained in a humidified CO2 incubator, with temperature, $CO_2$ concentration, and agitation controlled within ranges defined in the batch record. The preculture is incubated for ≤3 days until a minimum cell density of $\geq0.6\times10^6$ VC/mL and a culture viability of ≥50% are obtained. The preculture is expanded sequentially in a series of culture flasks and then culture bags as a mechanism to scale up for inoculation of the 100 L seed bioreactor. During the culture expansion phase, each incubation step takes ≤3 days to achieve passage conditions, which require a cell density of $\geq0.6\times10^6$ VC/mL and a culture viability of ≥80%. The seeding density for each passage is 0.2 to $0.5\times10^6$ VC/mL in culture flasks, and 0.2 to $0.6\times10^6$ VC/mL in culture bags. Each passage is sampled for viable cell density (VCD), culture viability, and microscopic examination. Prior to inoculation of the 100 L seed bioreactor, the preculture is sampled for bioburden.

Preculture expansions may be maintained for a maximum of 30 days post-thaw. Precultures not used within 30 days are discarded. Back-up precultures, expanded as described above and subject to the same in-process monitoring, control tests, and process parameters as the primary precultures, may be maintained and used to inoculate another 100 L seed bioreactor as needed When the preculture meets inoculum criteria, the contents of the culture bag(s) are transferred to the 100 L seed bioreactor containing CDH-A to target a seeding density of $\geq0.3\times10^6$ VC/mL. The seed bioreactor culture pH, temperature, and dissolved oxygen concentration are controlled within ranges defined in the batch record. The culture is expanded until a cell density of $\geq1.5\times10^6$ VC/mL and a culture viability of ≥80% are obtained. The culture is sampled for VCD, culture viability, and microscopic examination throughout the seed bioreactor process. Prior to inoculation of the 500 L production bioreactor, the culture is sampled for bioburden.

When the VCD of the seed bioreactor culture reaches $\geq1.5\times10^6$ VC/mL, the culture may be used to inoculate the 500 L production bioreactor. Alternatively, a portion of the culture can be drawn from the 100 L seed bioreactor and the remaining culture diluted with fresh medium. Following this "draw and fill" process, the culture is allowed to expand to sufficient cell density to inoculate the 500 L production bioreactor. The maximum duration of the 100 L seed bioreactor culture is 9 days post-inoculation.

Stage 2

Bioreactor Production

Figure 3:
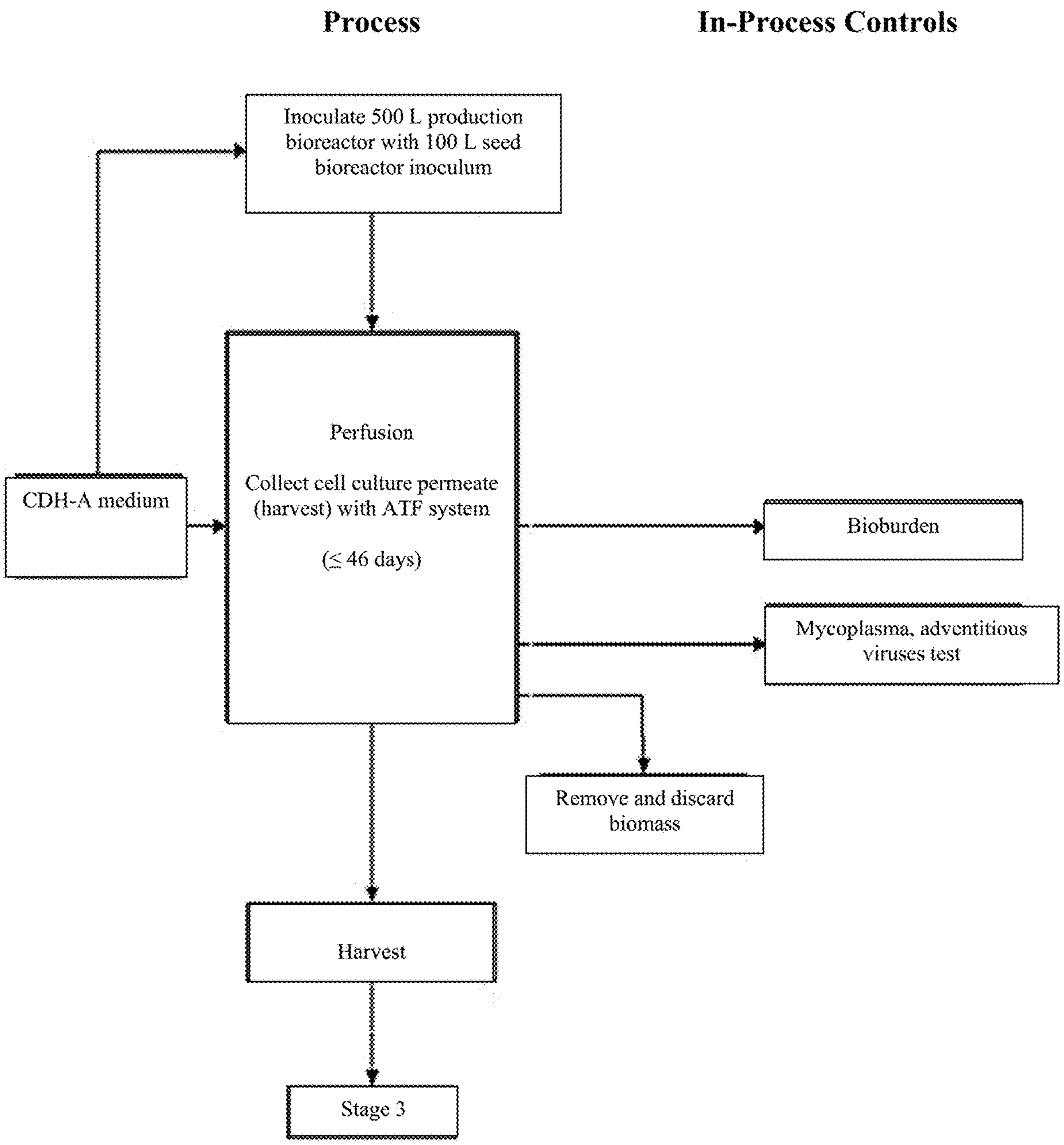
FIG. 3 shows a flow diagram of Stage 2 manufacturing process steps, including the in-process controls and process monitoring tests.

In Stage 2, cell culture is continuously perfused in a 500 L production bioreactor using an alternating tangential flow hollow fiber filter cell retention system (ATF system). Cell culture permeate (harvest) is collected from the ATF system while cells are returned to the bioreactor, and the culture is replenished with fresh medium. A flow diagram depicting the bioreactor production process is provided in FIG. 3.

Manufacturing Procedure

The inoculation of the 500 L production bioreactor is performed by transferring the contents of the 100 L seed bioreactor into the 500 L production bioreactor containing CD (chemically defined) hybridoma medium supplemented with 6 mM L-glutamine, 0.5 mg/L mycophenolic acid, 2.5 mg/L hypoxanthine, and 50 mg/L xanthine (CDH-A). The volume transferred must be sufficient to target a seeding density of $\geq0.3\times10^6$ viable cells (VC)/mL.

The culture is maintained at a temperature of 34 to 38° C., a pH of 6.8 to 7.6, and a dissolved oxygen (DO) concentration of 1 to 100%.

Continuous perfusion is initiated, and culture is drawn from the 500 L bioreactor into the ATF system to separate the cells from the permeate. The permeate is filtered through the 0.2 μm ATF filter and collected as harvest in bioprocess containers (BPCs). The cells are returned to the bioreactor, and fresh CDH-A is supplied to maintain a constant culture volume. Viable cell density (VCD), culture viability, pH, DO, temperature and immunoglobulin G (IgG) content are monitored during the production run. The perfusion rate is gradually increased in proportion to VCD until a target rate of approximately one bioreactor volume per day is reached. The perfusion rate is controlled, not to exceed 1.20 bioreactor volumes per day. Retention of the ATF system is monitored to facilitate shutdown of an ATF filter prior to the IgG retention across the filter exceeding 50%.

When the VCD within the 500 L bioreactor reaches $8.0\times10^6$ VC/mL or on day 10, whichever comes first, the pH target is lowered from 7.2 to 7.1. Biomass removal is initiated at either day 20 or when a VCD of $12.0\times10^6$ VC/mL is reached, whichever comes first. Biomass is removed from the 500 L production bioreactor into BPCs at a rate of up to 20% bioreactor volumes per day. Each harvest is sampled for bioburden.

The continuous perfusion cell culture operation in the 500 L production bioreactor continues for up to 46 days post-inoculation. At the end of production, the culture is sampled for mycoplasma and adventitious virus testing. Harvest may be stored for ≤30 days at 2 to 8° C. after disconnection from the bioreactor.

Description for Small-Scale Production of Ustekinumab Expressed in CHO Cells

Generation of CHO Cells Expressing Ustekinumab

The CHO cell line was originally created by T.T. Puck from the ovary of an adult Chinese hamster. CHO-K1 (ATCC® CCL-61) is a subclone of the parental CHO cell line that lacks the proline synthesis gene. CHO-K1 was also deposited at the European Collection of Cell Cultures, CHO-K1 (ECACC 85051005). A master cell bank (MCB) of CHO-K1, 024 M, was established at Celltech Biologics (now Lonza Biologics) and used for adaptation of CHO-K1 to suspension culture and serum-free medium. The adapted cell line was named CHOK1SV. The CHOK1SV cell line was further adapted in protein-free medium to create a MCB of cells referred to as 269-M. Cells derived from the 269-M MCB were transfected as described below to create the CHO cell lines expressing ustekinumab.

Cell lines were generated, expanded, and maintained in a humidified incubator at 37° C. and 5% $CO_2$ using cell culture plates and shake flasks. Routine seeding density in shake flasks was $3\times10^5$ viable cells per mL (vc/mL). All shake flask cultures were maintained at 130 revolutions per minute (rpm) with a 25 mm orbit and 96-deepwell (DW, Thermo Scientific, Waltham, MA, Cat. #278743) cultures were maintained at 800 rpm with a 3 mm orbit.

CHO clones expressing ustekinumab were created using media identified as MACH-1, an in-house developed, chemically-defined medium for CHO cell culture. The basal medium for the routine passage of the CHO host cell line was MACH-1 supplemented with 6 mM L-glutamine (Invitrogen, Carlsbad, CA, Cat. #25030-081). CHO cells transfected with the glutamine synthetase (GS) gene were grown in MACH-1+MSX unless otherwise noted, which is MACH-1 supplemented with 25 μM L-methionine sulfoximine (MSX, Sigma, St. Louis, MO, Cat. #M5379-1G) to inhibit glutamine synthetase function. For bolus fed-batch shake flask and bioreactor experiments, cells were cultured in MACH-1+F8, which is MACH-1 supplemented with 8 g/kg F8 (a supplement of proprietary growth enhancers) to further support cell growth and antibody production. Proprietary feed media were used in shake flask and bioreactor experiments.

The DNA encoding the genes of interest were cloned into a glutamine-synthetase (GS) double gene expression plasmid (Lonza Biologics). Expression of the heavy chain (HC) and light chain (LC) genes were driven by separate human cytomegalovirus (hCMV-MIE) promoters. The GS gene selection marker, driven by the Simian Virus SV40 promoter, allows for the selection of transfected cells in glutamine-free media in the presence of MSX.

Prior to each transfection, 1 aliquot of plasmid DNA, containing both the HC and LC coding regions of ustekinumab, was linearized by restriction enzyme digestion. A linearized 15 μg DNA aliquot was transfected into a $1\times10^7$ cell aliquot using the BTX ECM 830 Electro Cell Manipulator (Harvard Apparatus, Holliston, MA). Cells were electroporated 3 times at 250 volts with 15 millisecond pulse lengths and 5 second pulse intervals in a 4 mm gap cuvette. Transfected cells were transferred to MACH-1+L-glutamine in a shake flask and incubated for 1 day. Transfections were centrifuged, then resuspended in MACH-1+25 uM MSX for selection and transferred to shake flasks to incubate for 6 days.

Following chemical selection, cells were plated in a single cell suspension in custom glutamine-free Methocult medium containing 2.5% (w/v) methylcellulose in a Dulbecco's Modified Eagle's Medium (DMEM) base media (Methocult, StemCell Technologies, Inc., Vancouver, BC, Cat. #03899). The working solution also contained 30% (v/v) gamma-irradiated dialyzed fetal bovine serum (dFBS.IR, Hyclone, Logan, UT, Cat. #SH30079.03), 1× GS Supplement (SAFC, St. Louis, MO, Cat. #58672-100M), 1.5 mg animal component-free Protein G Alexa Fluor 488 conjugate (Protein G, Invitrogen, Carlsbad, CA, Cat. #C47010), 25 μM MSX, Dulbecco's Modified Eagle's Medium with F12 (DMEM/F12, Gibco/Invitrogen, Carlsbad, CA, Cat. #21331-020), and cell suspension.

Protein G recognizes human monoclonal antibodies and binds to the IgG that is secreted by the cells. The Protein G is conjugated to the fluorescent label Alexa Fluor 488, so that cell colonies secreting the most antibodies will show the highest levels of fluorescence. After incubation for 12 to 18 days, colonies with the highest fluorescence levels were picked into 100 μL phenol red-containing MACH-1+MSX in 96-well plates using a ClonePix FL colony picking instrument (Molecular Devices, Sunnyvale, CA) and incubated without shaking for 5-7 days. After 5-7 days, cells from the 96-well plate were expanded by adding to 50-100 μL phenol red-containing MACH-1+MSX in a 96DW plate (Thermo Scientific, Waltham, MA, Cat. #278743) and shaken at 800 rpm with a 3 mm orbit. The 96DW plates were fed and at 7 days post 96DW seeding were titered via Octet (ForteBio, Menlo Park, CA). The top 10 cultures corresponding to the highest batch 96DW overgrow titers were expanded to shake flasks in MACH-1+MSX, and frozen cell banks were created with cells suspended in in MACH-1+ MSX medium containing 10% DMSO.

Cell Culture for Small-Scale Production

As in large-scale production of ustekinumab expressed in Sp2/0 cells, preculture, cell expansion, and cell production are performed in Stages 1 and 2 for small-scale production of ustekinumab expressed in Chinese Hamster Ovary cells (CHO cells). In Stage 1, preculture is initiated from a single cell bank vial of transfected CHO cells expressing the HC and LC sequences of ustekinumab and the cells are expanded in culture flasks. The cells are cultured until the cell density and volume required for inoculation of a 10-L production bioreactor are obtained. In Stage 2, the cell culture is run in fed-batch mode in a 10-L production bioreactor. For the duration of the 15-day bioreactor run the culture is fed as required with concentrated glucose-based and amino acid-based feeds. At the completion of the production bioreactor run cell culture harvest is clarified to remove biomass and filtered for further processing.

Purification for Small-Scale Production

The purification steps for small-scale production of ustekinumab were identical to the large-scale manufacturing process, except the Stage 8 virus filtration step was omitted for small-scale production. In brief, for small-scale production, purification of ustekinumab from the cell culture harvest is performed in Stages 3 through 7 by a combination of affinity and ion exchange chromatography steps and steps to inactivate or remove potential virus contamination (solvent/detergent treatment and virus removal). In Stage 3, harvest and/or pooled harvest is clarified and purified using Protein A affinity chromatography. The resultant direct product capture (DPC) eluate is frozen until further processing. DPC eluates are filtered and pooled in Stage 4 following thaw, and subsequently treated in Stage 5 with tri-n-butyl phosphate (TNBP) and polysorbate 80 (PS 80) to inactivate any lipid-enveloped viruses potentially present.

In Stage 6, TNBP and PS 80 reagents and impurities are removed from the ustekinumab product using cation exchange chromatography. The ustekinumab product is further purified using anion exchange chromatography in Stage 7 to remove DNA, potentially present viruses, and impurities. As noted above, Stage 8 filtering through a virus retentive filter was omitted from the CHO derived ustekinumab product purification process.

Final preparation of ustekinumab pre-formulated bulk (PFB) and formulated bulk (FB) is performed in Stages 9 and 10, respectively (references to large-scale stages). In Stage 9, the ultrafiltration step concentrates the ustekinumab product, and the diafiltration step adds the formulation excipients and removes the in-process buffer salts. Polysorbate 80 is added to the ustekinumab PFB in Stage 10 to obtain the FB and the FB is filtered into polycarbonate containers for frozen storage.

Methods

Methods for Determining Viable Cell Density (VCD) and % Viability

Total cells per/ml, viable cells/ml (VCD), and % viability are typically determined with a Beckman Coulter Vi-CELL-XR cell viability analyzer using manufacturer provided protocols, software and reagents. Alternatively, a CEDEX automated cell counting system has also been used. It should also be noted, however, that other methods for determining VCD and % viability are well known by those skilled in the art, e.g., using a hemocytometer and trypan blue exclusion.

Bioactivity Assay

The bioactivity of ustekinumab is determined by neutralization of IL-12 induced interferon-gamma (IFN-γ) production by an IL-12-responsive human natural killer cell line, NK-92 MI (ATCC® CRL-2408). Ustekinumab binds the p40 subunit of IL-12 and impedes the interaction with the IL-12Rβ1 on the cell surface of NK cells. This results in the blockade of IL-12 mediated production of IFN-γ (Aggeletopoulou I, et al. Interleukin 12/interleukin 23 pathway: Biological basis and therapeutic effect in patients with Crohn's disease. *World J Gastroenterol.* 2018;24(36):4093-4103). In brief, the assay method involves incubating NK-92MI cells with recombinant human IL-12 (rhIL-12) and comparing the levels of IFN-γ secreted by the cells in the presence and absence of ustekinumab. The levels of IFN-γ are quantified with an enzyme-linked immunosorbent assay (ELISA) using an anti-IFN-γ antibody (see, e.g., Jayanthi S, et al. Modulation of Interleukin-12 activity in the presence of heparin. *Sci Rep.* 2017;7(1):5360).

Methods for Determining Oligosaccharide Composition

Oligosaccharide Composition by HPLC

Figure 4:
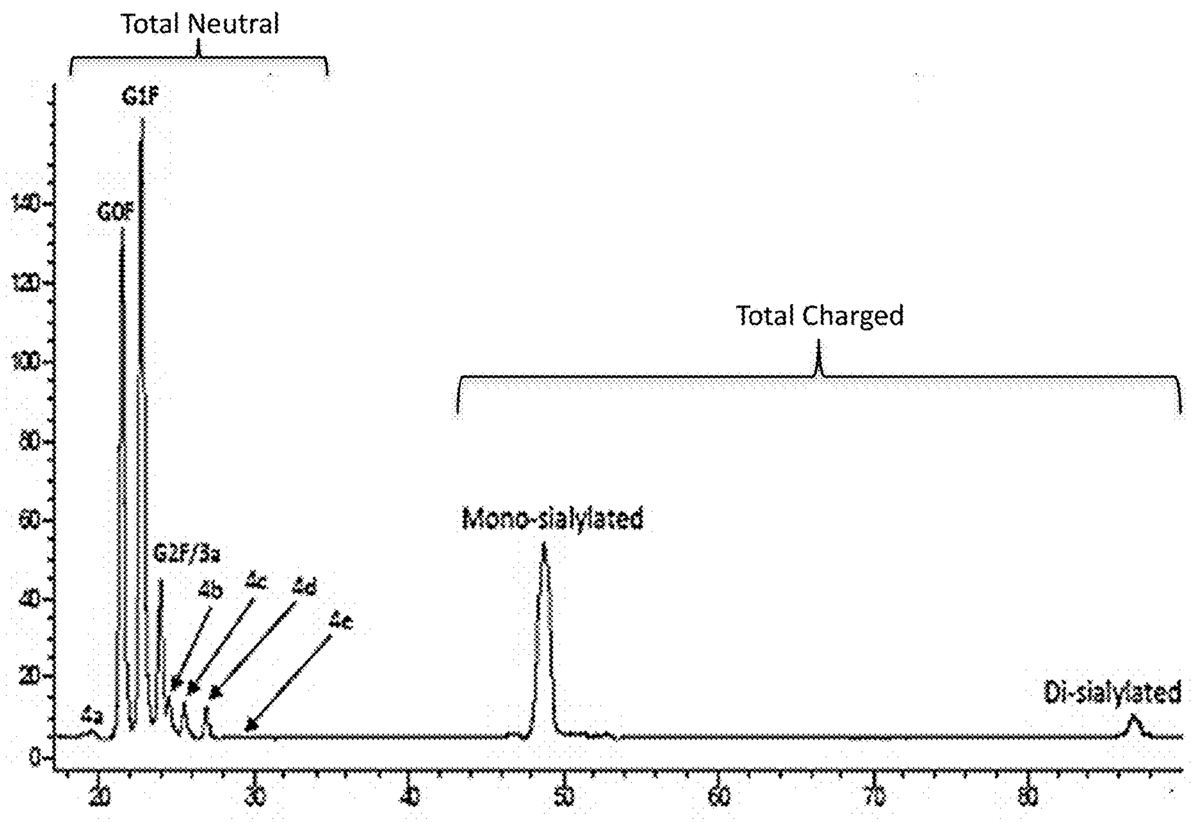
FIG. 4 shows a representative HPLC chromatogram for oligosaccharide analysis of ustekinumab produced in Sp2/0 cells.

The N-linked oligosaccharide composition of ustekinumab is determined with a normal phase anion exchange HPLC method with fluorescent detection using an Agilent 1100/1200 Series HPLC System with Chemstation/Chemstore software. To quantitate the relative amounts of glycans, the N-linked oligosaccharides are first cleaved from the reduced and denatured test article with N-glycanase (PNGase F). The released glycans are labeled using anthranilic acid, purified by filtration using 0.45-μm nylon filters, and analyzed by HPLC with fluorescence detection. The HPLC chromatogram serves as a map that can be used to identify and quantitate the relative amounts of N-linked oligosaccharides present in the sample. Glycans are identified by co-elution with oligosaccharide standards and by retention time in accordance with historical results from extensive characterizations. A representative HPLC chromatogram for ustekinumab is shown in FIG. 4.

The amount of each glycan is quantitated by peak area integration and expressed as a percentage of total glycan peak area (peak area %). Results are reported for G0F, G1F, G2F, total neutrals, and total charged glycans. Other neutrals are the sum of all integrated peaks between 17 and 35 minutes, excluding the peaks corresponding to G0F, G1F and G2F. Total neutral glycans is the sum of G0F, G1F, G2F and the other neutrals. Total charged glycans is the sum of all mono-sialylated glycan peaks eluting between 42 and 55 minutes and all disialylated glycan peaks eluting between 78 and 90 minutes.

A mixture of oligosaccharide standards (G0F, G2F, G2F+N-acetylneuraminic acid (NANA) and G2F+2NANA) is analyzed in parallel as a positive control for the labeling reaction, as standards for peak identification, and as a measure of system suitability. Reconstituted oligosaccharides from Prozyme, G0F (Cat. No. GKC-004301), G2F (Cat. No. GKC-024301), SA1F (Cat. No. GKC-124301), and SA2F (Cat. No. GKC-224301), or equivalent, are used as reference standards. A method blank negative control and pre-labeled G0F standard are also run for system suitability purposes. The following system suitability and assay (test article) acceptance criteria are applied during the performance of the oligosaccharide mapping procedure in order to yield a valid result:

System Suitability Criteria

- Resolution (USP) between the G0F and G2F peaks in the oligosaccharide standard must be ≥3.0.
- Theoretical plate count (tangent method) of the G0F peak in the oligosaccharide standards must be ≥5000.
- The total glycan peak area for the ustekinumab reference standard must be ≥1.5 times of the major glycan peak area of the pre-labeled G0F.
- If any reference standard glycan peak is off-scale, the reference standard is re-injected with less injection volume.
- The retention time of G0F peak in the ustekinumab reference standard must be within 0.4 min of the G0F retention time in the oligosaccharide standards.

Assay Acceptance Criteria

- The method blank must have no detectable peaks that co-elute with assigned oligosaccharide peaks in ustekinumab.
- The total glycan peak area of each test article must be ≥1.5 times the major glycan peak area of the pre-labeled G0F standard.
- If any sample glycan peak is off-scale, that sample is re-injected with less injection volume, together with pre-labeled G0F, the oligosaccharide standards, Method Blank and reference standard with normal volume.
- The retention time for the G0F peak in each test article must be within 0.4 min of the retention time for the G0F peak in the oligosaccharide standards.
- If the assay fails to meet any acceptance criteria, the assay is invalidated

Oligosaccharide Composition by IRMA

The IdeS-RMA (IRMA) method allows differentiation between major glycoforms by Reduced Mass Analysis (RMA) after the enzymatic treatment of immunoglobulin G (IgG) with FabRICATOR®, an IgG degrading enzyme of *Streptococcus pyogenes* (IdeS) available from Genovis AB (SKU: A0-FR1-050). See also, for example, U.S. Pat. No. 7,666,582. Reduced Mass Analysis (RMA) involves disulfide bond reduction of antibodies followed by the intact mass analysis of the heavy chain of the antibody and its attached glycan moieties. Some antibodies show a large degree of heterogeneity due to the presence of N-terminal modifications such as pyroglutamate formation and carboxylation. Consequently, disulfide reduction and heavy chain mass measurement results in a complex pattern of deconvoluted peaks. Therefore, in some applications, proteolytic generation of antibody fragments is desired over generation of light and heavy chains using reduction agents such as dithiothreitol (DTT). Traditionally papain and pepsin are used to generate antibody fragments all of which are laborious processes. Cleavage of IgG with pepsin requires extensive optimization and it is done at low acidic pH. Papain needs an activator and both F(ab')2 and Fab can be obtained depending on the reaction conditions resulting in a heterogeneous pool of fragments. These drawbacks can be circumvented by using the novel enzyme, FabRICATOR®.

The cleavage procedure is very fast, simple, and importantly no optimization is needed. It is performed at neutral pH generating precise F(ab')2 and Fc fragments. No further degradation or over-digestion is observed as is commonly associated with other proteolytic enzymes like pepsin or papain. Importantly, as FabRICATOR® cleaves just C-terminally of the disulfide bridges in the heavy chain, no reduction step is required and an intact F(ab')2 and two residual Fc fragments are obtained.

Definitions

- H: hexose (mannose, glucose, and galactose)
- Man5: mannose 50
- N: N-acetylhexosamine (N-acetylglucosamine and N-acetylgalactosamine)
- F: fucose
- S: sialic acid (N-acetylneuraminic acid (NANA) and N-glycolylneuraminic acid (NGNA))
- G0: asialo-agalacto-afucosylated biantennary oligosaccharide
- G0F: asialo-agalacto-fucosylated biantennary oligosaccharide
- G1: asialo-monogalactosylated-afucosylated biantennary oligosaccharide
- G1F: asialo-monogalactosylated-fucosylated biantennary oligosaccharide
- G2: asialo-digalactosylated-afucosylated biantennary oligosaccharide
- G2F: asialo-digalactosylated-fucosylated biantennary oligosaccharide
- GlcNAc: N-Acetyl-D-Glucosamine
- Lys: Lysine
- −Lys: Truncated heavy chain (no C-terminal Lysine residue present)
- +Lys: Heavy chain containing C-terminal Lysine
- ppm: parts per million

Equipment

- Thermo Scientific Q Exactive (Plus) mass spectrometer
- Agilent 1200 HPLC system
- Applied Biosystems POROS R2/10 2.1 mmD×100 mmL column
- Thermo Scientific Q Exactive Tune software
- Thermo Scientific Protein Deconvolution software
- Analytical balance capable of weighing 0.01 mg
- Vortex mixer, any suitable model
- Water bath or heating block, any suitable model
- Calibrated Thermometer −10 to 110° C., any suitable model
- Calibrated Pipettes
- Microcentrifuge, any suitable model

Procedure

IdeS Digestion of Samples

- samples (equal to 50 μg IgG).
- add 1 μl (50 units) of IdeS enzyme to 50 μg of IgG, vortex briefly, spin down, and incubate at 37° C. for 30 minutes (stock enzyme@5000 units per 100 μl. 1 unit of enzyme fully digests 1 μg of IgG in 30 minutes at 37° C.)
- spin down samples and transfer to LC-MS vials, and load sample vials into Agilent 1200 autosampler

LC-MS Method

Solution Preparation

- Mobile phase A (0.1% Formic Acid (FA) in ultrapure water)—Add 999 mL of ultrapure water to a 1 L HPLC Mobile phase bottle, add 1 mL FA and stir. This solution can be stored at RT for 2 months.
- Mobile phase B (0.1% FA, 99.9% acetonitrile)—Add 999 mL of acetonitrile to a 1 L HPLC Mobile phase bottle, add 1 mL FA and stir. This solution can be stored at RT for 2 months.

LC Method

- Column: Applied Biosystems POROS R2/10 2.1 mmD× 100 mmL
- Column temperature: 60° C.
- Auto sampler temperature: 4° C.
- Flow rate: 300 L/min
- Injection volume: 5 μL
- Mobile phase A: 0.1% FA in ultrapure water
- Mobile phase B: 0.1% FA in acetonitrile

TABLE 1

LC Gradient Table

| Time (min) | % Mobile phase B |
|---|---|
| 0.0 | 10 |
| 6.0 | 30 |
| 11.9 | 42 |
| 12.0 | 95 |
| 15.9 | 95 |
| 16.0 | 10 |
| 21.0 | 10 |

MS Method

Scan Parameters

- Scan type: Full MS
- Scan range: 700 to 3500 m/z
- Fragmentation: In-source CID 35.0 e V
- Resolution: 17500
- Polarity: Positive
- Lock masses: On, m/z 445.12002
- AGC target: 3e6
- Maximum injection time: 250

HESI Source

- Sheath gas flow rate: 32
- Aux gas flow rate: 7
- Sweep gas flow rate: 0
- Spray voltage (|kV|): 4.20
- Capillary temp. (° C.): 280
- S-lens RF level: 55.0
- Heater temp. (° C.): 80

Data Analysis

Figure 5:
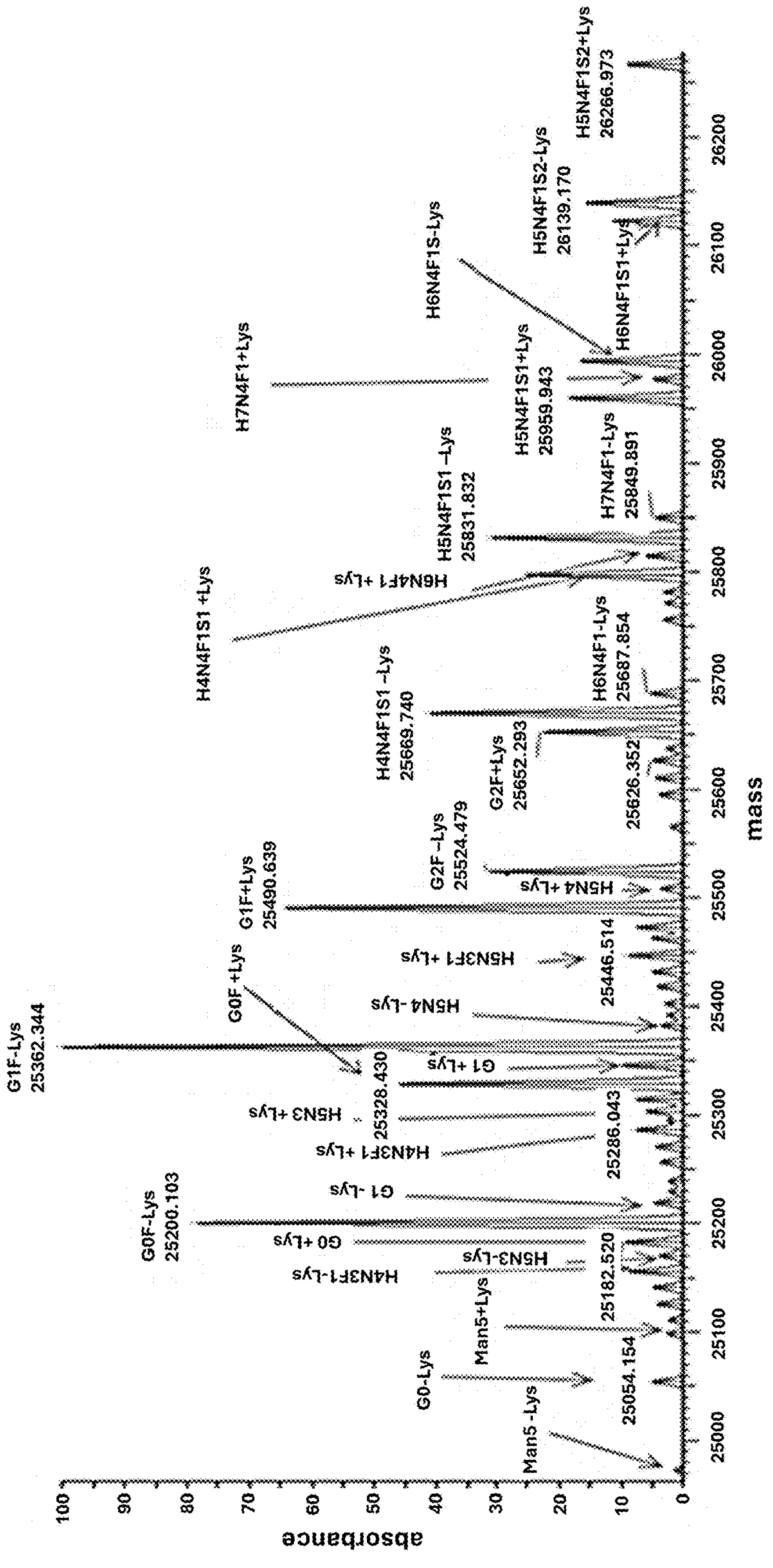
FIG. 5 shows a representative deconvoluted mass spectrum for IRMA analysis of ustekinumab produced in Sp2/0 cells.

The relative content of each detected glycan species is recorded based on analysis of deconvoluted mass spectra. FIG. 5 shows a representative deconvoluted mass spectrum for IRMA analysis of ustekinumab produced in Sp2/0 cells. The major structures determined by IRMA analysis include, e.g., G0 (H3N4), G0F (H3N4F1), G1F-GlcNAc (H4N3F1), H5N3, G1 (H4N4), H5N3F1, G1F (H4N4F1), G2 (H5N4), G2F (H5N4F1), G1FS (H4N4F1S1), H6N4F1, G2FS (H5N4F1S1), H7N4F1, H6N4F1S1, G2FS2 (H5N4F1S2). The percentage of each of these structures is monitored. The measured peak intensity represents the percentage of each structure after normalization (% of Total Assigned). Glycans of which the observed mass is outside the 100 ppm mass deviation threshold are not included in the calculations, e.g., (*G1F-GlcNAc-Lys, *H5N3-Lys, *G1-Lys, *H5N3F1-Lys, and *G2-Lys). As noted, these are indicated with an asterisk ("*"). Also, Man5-Lys is not always detected in the spectra since it has a very low intensity, nevertheless it is considered and included into the calculations when present. The percentage of a glycan is calculated as detected on both isoforms of the Fc fragment with and without terminal Lysine, e.g., percentage G0F is (% G0F-Lys+% G0F+Lys). Structures detected on only one of the heavy chain isoforms are indicated with a double asterisk (""), e.g., G1F-GlcNAc-Lys, H5N3-Lys, H5N4-Lys, and **H5N3F1+Lys. Most of these structures are low abundant and cannot be resolved from adjacent peaks with higher intensities or are below the detection capabilities of the method.

*Note: Differences between the HPLC and IRMA methods (e.g., see Table 2 below) may result from co-elution of species in HPLC and possibly underestimation of some sialylated species by IRMA because some of the intensities are very close to the limit of detection capabilities of the IRMA method.

TABLE 2

Glycan abundance comparison for IRMA and HPLC for representative ustekinumab sample produced in Sp2/0 cells

| Glycan Group | IRMA % | HPLC % |
|---|---|---|
| G0F | 21.6 | 25.0 |
| G1F | 28.5 | 33.2 |
| G2F | 9.2 | 7.8 |
| Other neutral oligosaccharides | 11.4 | 5.9 |
| Total neutral oligosaccharides | 70.7 | 71.9 |
| Monosialylated | 25.0 | 25.9 |
| Disialylated | 4.3 | 2.2 |
| Total charged oligosaccharides | 29.3 | 28.1 |

Capillary Isoelectric Focusing

Figure 6:
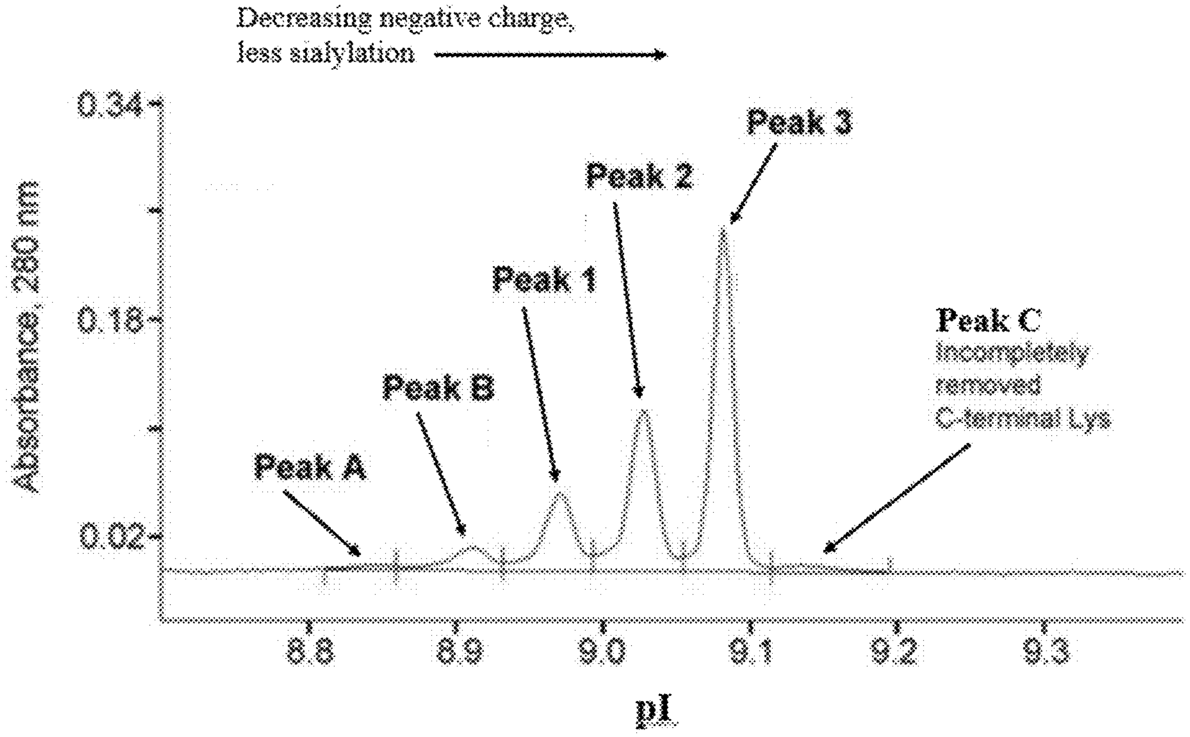
FIG. 6 shows a representative cIEF electropherogram profile of ustekinumab expressed in Sp2/0 cells. A graphic representing the general relationship between cIEF peaks and decreasing negative charge/degree of sialylation is also shown and Peaks A, B, 1,2, 3, and C are labeled.
Figure 9:
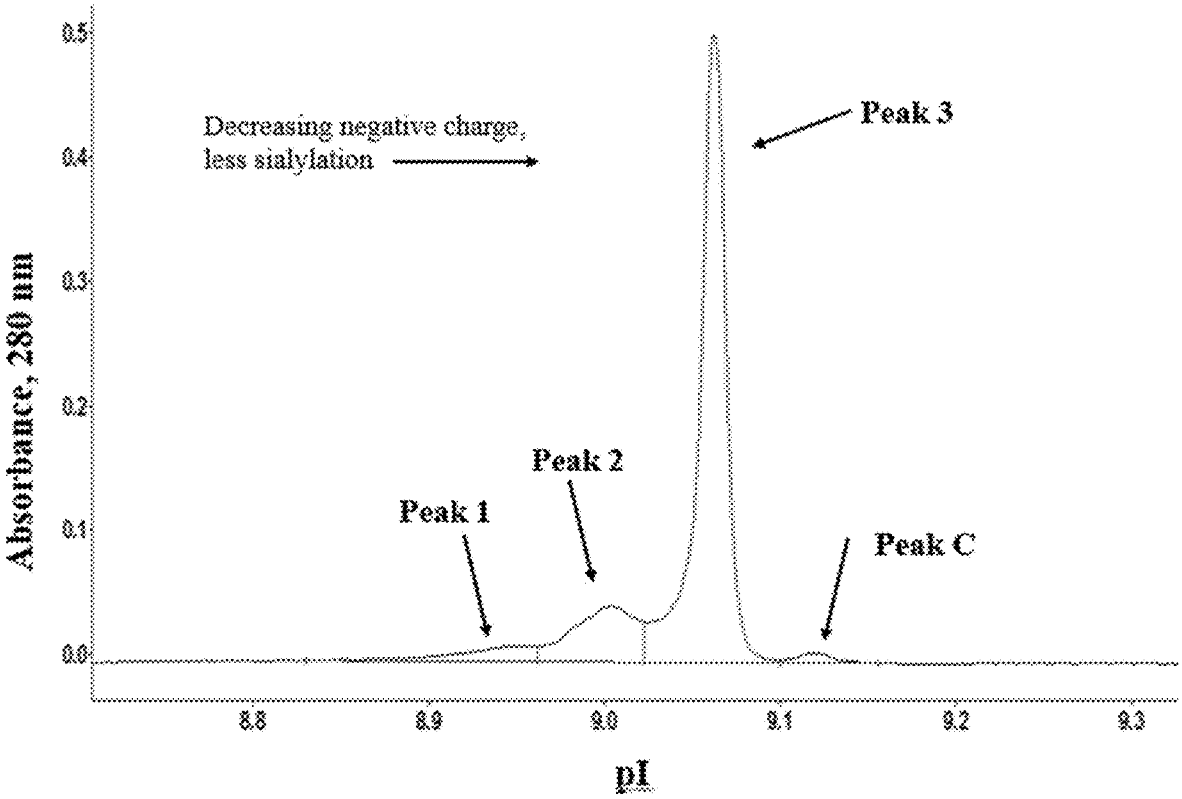
FIG. 9 shows a representative cIEF electropherogram profile of ustekinumab expressed in CHO cells. A graphic representing the general relationship between cIEF peaks and decreasing negative charge/degree of sialylation is also shown and Peaks 1, 2, 3, and C are labeled.

Capillary isoelectric focusing (cIEF) separates proteins on the basis of overall charge or isoelectric point (pI). The method is used to monitor the distribution of charge-based isoforms in ustekinumab. Unlike the gel-based IEF procedures, cIEF provides a quantitative measure of the charged species present. In addition, cIEF shows increased resolution, sensitivity, and reproducibility compared to the gel-based method. The assay is performed on a commercially available imaging cIEF analyzer equipped with an autosampler able to maintain sample temperature≤10.5° C. in an ambient environment of ≤30° C., such as the Alcott autosampler (GP Instruments, Inc.). The analysis employs an inner wall-coated silica capillary without an outer wall polyimide coating to allow for whole column detection. In addition, an anolyte solution of dilute phosphoric acid and methylcellulose, a catholyte solution of sodium hydroxide and methylcellulose, and a defined mixture of broad range (pH 3-10) and narrow range (pH 8-10.5) ampholytes are used. The assay employs a pre-treatment of both test articles and Reference Standard (RS) with carboxypeptidase B (CPB) which removes the heavy chain C-terminal lysine and eliminates ambiguities introduced by the presence of multiple C-terminal variants. A representative cIEF electropherogram of ustekinumab expressed in Sp2/0 cells is shown in FIG. 6 and representative cIEF electropherogram of ustekinumab expressed in CHO cells is shown in FIG. 9.

Before each analysis, the autosampler temperature set-point is set to 4° C. and the autosampler is pre-cooled for at least 30 minutes and the ambient room temperature of the lab is maintained ≤30° C. The pre-treated test article and RS, sample vials, vial inserts, the reagents used in the assay including purified water, the parent solution containing N,N,N',N'-Tetramethylethylenediamine (TEMED) (which optimizes focusing within the capillary), ampholytes, pI 7.6 and 9.5 markers for internal standards and methylcellulose (MC) are kept on ice for at least 30 minutes before starting sample preparation. The samples are prepared on ice and the time of addition of the parent solution is recorded and exposure to TEMED is controlled. The assay must be completed within 180 minutes after this addition. System suitability controls are injected once, and test articles and RS are injected twice following the sequence table below (Table 3):

TABLE 3

Sample Running Sequence

| Sample Name | Sample Vial Position | Number of Injections |
|---|---|---|
| System Suitability | 1 | 1 |
| Blank | 2 | 1 |
| CPB Control | 3 | 1 |
| CPB Treated RS | 4 | 2 |
| CPB Treated Sample 1 | 5 | 2 |
| CPB Treated RS | 6 | 2 |

After the samples are injected into the capillary by a syringe pump, an electric field (3 kV) is applied across the capillary for 8 min, forming a pH gradient, and charge-based isoforms of ustekinumab are separated according to their isoelectric point (pI). The protein isoforms in the capillary are detected by imaging the entire capillary at 280 nm, and the data are presented in the form of an electropherogram as a function of pI value vs A280. Values for pI are assigned by comparison to the internal pI standards (pI 7.6 and 9.5) using the instrument software, and peak areas are determined from the electropherogram using standard data acquisition software. The average pI and average peak area percentage from duplicate injections of all peaks≥LOD, the ΔpI value compared to Reference Standard, and percent area peaks are reported.

Introduction to Manufacturing Control Strategies

During large-scale commercial production, manufacturing control strategies are developed to maintain consistent drug substance (DS) and drug product (DP) characteristics of therapeutic proteins (e.g., therapeutic antibodies like ustekinumab), with regard to oligosaccharide profile, bioactivity (potency), and/or other characteristics of the DS and DP (e.g., See characteristics identified in Table 4 and Table 5). For example, ustekinumab glycosylation is monitored as an in-process control for formulated bulk (FB) at Stage 10 of the manufacturing process, with upper and lower specifications in place for mean % total neutral oligosaccharides, % total charged oligosaccharides, and % individual neutral oligosaccharide species, G0F, G1F, and G2F. As used herein, the terms "drug substance" (abbreviated as "DS") and "drug product" (abbreviated as "DP") refer to compositions for use as commercial drugs, for example in clinical trials or as marketed drugs. A DS is an active ingredient that is intended to furnish pharmacological activity or other direct effect in the diagnosis, cure, mitigation, treatment, or prevention of disease or to affect the structure or any function of the human body. The formulated bulk (FB) produced in the manufacturing process is the drug substance (DS). A DP (also referred to as a medicinal product, medicine, medication, or medicament) is a drug used in the diagnosis, cure, mitigation, treatment, or prevention of disease or to affect the structure or any function of the human body. The DP is the DS that has been prepared as the medicinal product for sale and/or administration to the patient.

As shown in Table 4, there are only very small differences in % Monomer, % Purity, and % Bioactivity for ustekinumab produced in Sp2/0 cells and CHO cells. However, there are substantial differences in the cIEF profiles that are caused primarily by differences in the oligosaccharide profile of ustekinumab produced in Sp2/0 cells and CHO cells. For a comparison of cIEF profiles for ustekinumab produced in Sp2/0 cells and CHO cells, see also, e.g., FIG. 6 and FIG. 9.

TABLE 4

Representative comparison of selected ustekinumab characteristics expressed in Sp2/0 cells and CHO cells

| Test | Parameter | Sp2/0 Cells | CHO Cells |
|---|---|---|---|
| DW-SE-HPLC | % Monomer | 99.75% | 99.40% |
| | % Aggregate | 0.23% | 0.57% |
| | % Fragment | <LOD | <LOD |
| cSDS Reduced | % Purity | 98.9% | 98.2% |
| cSDS Non-Reduced | % Purity | 98.9% | 97.3% |
| Bioactivity | % Bioactivity | NA | 96%[a] |
| cIEF | peak A | 0.6% | <LOD |
| | peak B | 3.9% | <LOD |
| | peak 1 | 12.6% | 5.5% |
| | peak 2 | 28.7% | 15.8% |
| | peak 3 | 53.6% | 76.9% |
| | peak C | 0.8% | 1.7% |

<LOD—below limit of detection
NA—Not Applicable for reference material produced in Sp2/0 cells
[a]Compared to reference material expressed in Sp2/0 cells

Oligosaccharide Profile of Ustekinumab

Figure 7:
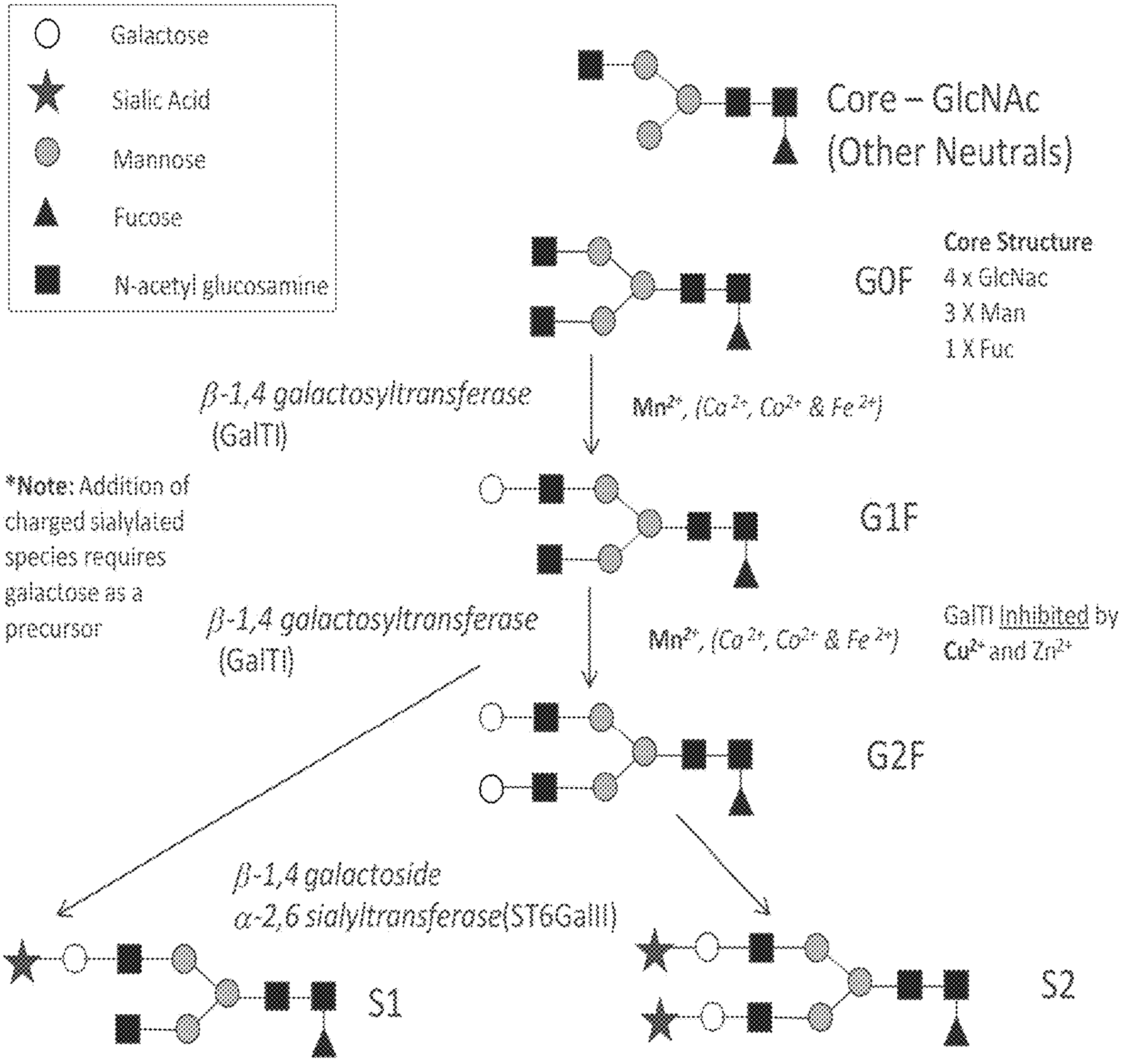
FIG. 7 shows a diagrammatic overview of some of the primary N-linked oligosaccharide species in ustekinumab IgG. The role of some of the enzymes in the glycosylation maturation process and role of some divalent cations (e.g. $Mn^{2+}$ as a co-factor and $Cu^{2+}$ as an inhibitor of GalTI) are also shown (see, e.g., *Biotechnol Bioeng.* 2007 Feb. 15;96 (3):538-49; *Curr Drug Targets.* 2008 April;9(4):292-309; J Biochem Mol Biol. 2002 May 31;35(3):330-6). Note that species with terminal sialic acid (S1 and S2) are charged species and species lacking the terminal sialic acid (G0F, G1F, and G2F) are neutral species, but generation of charged species depends on the presence of the galactose in G1F and G2F added by the GalT1 enzyme.

Ustekinumab is N-glycosylated at a single site on each heavy chain, on asparagine 299. These N-linked oligosaccharide structures can be any in a group of biantennary oligosaccharide structures linked to the protein through the primary amine of the asparagine residue, but on ustekinumab they consist primarily of biantennal core-fucosylated species, with galactose and sialic acid heterogeneity. Major individual oligosaccharide species include, e.g., "G0F", an asialo, agalacto core-fucosylated biantennary glycan, "G1F", an asialo, mono-galacto core-fucosylated biantennary glycan, and "G2F", an asialo, di-galacto core-fucosylated biantennary glycan. A diagrammatic overview of some of the primary N-linked oligosaccharide species in ustekinumab IgG is shown in FIG. 7. The role of some of the enzymes in the glycosylation maturation process, including roles of some divalent cations (e.g., $Mn^{2+}$ and $Cu^{2+}$) in these enzymatic processes are also shown.

HPLC is an analytical procedure that is deployed to analyze glycosylation of ustekinumab during the manufacturing method. For analysis by HPLC, the glycans are first enzymatically cleaved from the heavy chain and then labeled with a fluorescent label to allow detection. In the method, uncharged peaks for G0F, G1F and G2F can be distinguished, as well as a subset of smaller neutral peaks. Furthermore, peaks for differentially sialylated material can also be observed (FIG. 4). Another method for oligosaccharide analysis is IRMA, a reduced mass analysis (RMA) method using Immunoglobulin G (IgG) degrading enzyme of Streptococcus pyogenes (IdeS) that allows differentiation between major glycoforms after the enzymatic treatment of IgGs. FIG. 5 shows a representative deconvoluted mass spectrum for IRMA analysis of ustekinumab produced in Sp2/0 cells. For ustekinumab, there is also a direct relationship between the degree of sialylation on the oligosaccharide structures and the charge heterogeneity as determined by cIEF, IRMA, or HPLC (see, e.g., FIG. 4, FIG. 5, FIG. 6, FIG. 8, and FIG. 9).

Controlling Oligosaccharide Profile

Controlling the oligosaccharide profile is critical because changes in the oligosaccharide profile of a recombinant monoclonal antibody can significantly affect antibody biological functions. For example, biological studies have shown that the distribution of different glycoforms on the Fc region can significantly impact antibody efficacy, stability, and effector function (*J. Biosci. Bioeng.* 2014 117(5):639-644; *Bio-Process Int.* 2011, 9(6):48-53; *Nat. Rev. Immunol.* 2010, 10(5):345-352). In particular, afucosylation (*J. Mol. Biol.* 368:767-779) and galactosylation (*Biotechnol. Prog.* 21:1644-1652) can play a huge role in the antibody-dependent cell-mediated cytotoxicity (ADCC) and complement-dependent cytotoxicity (CDC), two important mechanisms by which antibodies mediate killing target cells through the immune function. In addition, high mannose levels have been shown to adversely affect efficacy by increasing clearance of the antibody (*Glycobiology.* 2011, 21(7):949-959) and sialic acid content can affect anti-inflammatory activity (*Antibodies.* 2013 2(3):392-414). As a result of these biological consequences from changes in the oligosaccharide profile, regulatory agencies require control of the antibody glycosylation pattern to ensure adherence to lot release specifications for a consistent, safe and effective product.

Oligosaccharide Profile—Effects from Expression in Different Cells

Two commonly used rodent host cell lines for the recombinant expression of antibodies are Chinese Hamster Ovary cells (CHO) and mouse myeloma cells (e.g., Sp2/0 cells). CHO cells express recombinant antibodies which can be virtually devoid of sialic acid glycan and the glycans can be up to 99% fucosylated. In contrast, mouse myeloma cells express recombinant antibodies that can contain up to 50% sialic acid and generally have less fucose. These differences can have significant effects on antibody activity in vivo, e.g., it has been shown that such differences can affect the structure of the Fc-portion of the molecule and thereby alter antibody effector functions such as antibody-dependent cellular cytotoxicity (ADCC) and complement-dependent cytotoxicity (CDC) (see, e.g., U.S. Pat. No. 8,975,040). For example, reduced ADCC activity has been noted with increased sialylated (charged) Fc glycans (Scallon et al., *Mol Immunol* 2007; 44:1524-34) and increased ADCC activity has been reported for antibodies that were deficient in fucose (Shields et al., *J Biol Chem.* 2002;277:26733-26740; Shinkawa et al., *J Biol Chem.* 2003;278:3466-3473).

In addition, antibodies produced in CHO and Sp2/0 cells can have significant differences in the levels of two glycan epitopes, galactose-α-1,3-galactose (α-gal) and the sialylated N-glycan Neu5Gc-α-2-6-galactose (Neu5Gc). For example, it has been shown that CHO cells can express antibodies with undetectable or only trace levels of α-Gal and Neu5Gc, while Sp2/0 cells can express much higher levels of the two glycan structures (Yu et al., *Sci Rep.* 2016 Jan. 29;7:20029). In contrast, humans are genetically deficient in the gene for biosynthesizing α-gal and the gene responsible for production of Neu5Gc is irreversibly mutated in all humans. As a result, α-Gal and Neu5Gc are not produced in humans. Furthermore, the presence of these non-human glycan epitopes on therapeutic antibodies can cause undesirable immune reactions in certain human populations because of higher levels of pre-existing antibodies to α-Gal and Neu5Gc. For example, anti-α-gal IgE mediated anaphylactic responses have been reported for Cetuximab (Chung, C. H. et al., *N Engl J Med.* 2008 Mar. 13;358 (11):1109-17) and the presence of circulating anti-Neu5Gc antibodies has been reported to promote clearance of Cetuximab (Ghaderi et al., *Nat Biotechnol.* 2010 August;28 (8): 863-7).

It has also been reported that ustekinumab expressed in Sp2/0 cells contains higher levels of Neu5Gc compared to a number of other antibodies. Western blot analysis showed that anti-Neu5Gc antibody preparations highly mono-specific for Neu5Gc bound to ustekinumab, but not to ustekinumab treated with PNGase F, which removes nearly 100% of the N-glycan (Yu et al., *Sci Rep.* 2016 Jan. 29;7:20029). Further analysis also showed that anti-Neu5Gc antibody preparations could not bind ustekinumab with only one Neu5Gc (mono-sialylated on one Fc region) but could bind antibodies with two to four Neu5Gc. It was not determined if the anti-Neu5Gc antibody could bind two Neu5Gc located on two different Fc regions of the same antibody (monosialylated on both Fc regions) or only to a disialylated N-glycan on one Fc region of an antibody, but regardless of their distribution it was determined that at least two Fc Neu5Gc residues are required for binding to the anti-Neu5Gc antibody.

Figure 8:
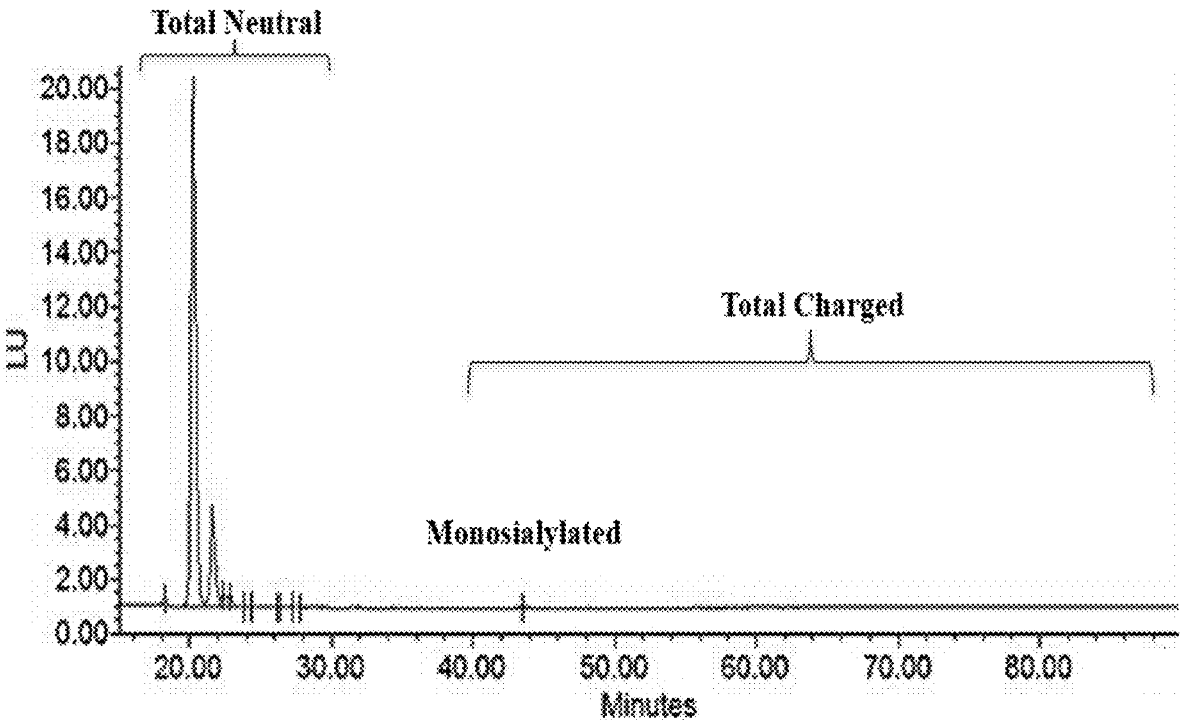
FIG. 8 shows a representative HPLC chromatogram for oligosaccharide analysis of ustekinumab produced in CHO cells. Hash marks indicate all peaks above baseline identified by the analysis software and brackets with labels indicate groups of peaks representing Total Neutral, Total Charged, and Monosialylated oligosaccharide species.

Oligosaccharide Profile of Ustekinumab Expressed in Sp2/0 Cells and CHO Cells Compiled HPLC data from multiple commercial production runs of ustekinumab showed that DS or DP produced in Sp2/0 cells comprises total neutral oligosaccharide species≥64.8% to ≤85.4%, total charged oligosaccharide species≥14.4% to ≤35.6%, and individual neutral oligosaccharide species G0F≥11.5% to ≤40.2%, G1F≥29.9% to ≤40.6%, and G2F≥4.1% to ≤11.3%. Furthermore, the peak 3 area % of the capillary isoelectric focusing (cIEF) electropherogram of ustekinumab produced in Sp2/0 cells is ≥39.8% to ≤64.4%. As shown in Table 5 and Table 6, based on IRMA or HPLC analysis, ustekinumab produced in CHO cells has a very different oligosaccharide profile compared to ustekinumab produced in Sp2/0 cells for total neutral, total charged, and individual neutral oligosaccharide species G0F, G1F, and G2F. These differences are apparent in representative HPLC chromatograms for ustekinumab produced in Sp2/0 cells and CHO cells, as shown in FIG. 4 and FIG. 8, respectively. Compared to ustekinumab produced in Sp2/0 cells, the oligosaccharide profile for ustekinumab produced in CHO cells is shifted toward very low levels of charged glycans and higher levels of neutral glycans, that are predominantly G0F. The oligosaccharide profile for ustekinumab produced in CHO cells comprises total neutral oligosaccharide species>99.0%, total charged oligosaccharide species<1.0%, and individual neutral oligosaccharide species G0F>70.0%, G1F<20.0%, and G2F<5.0%. The peak 3 area % of the capillary isoelectric focusing (cIEF) electropherogram of ustekinumab produced in CHO cells is >70.0%. Furthermore, no disialylated glycan species were detected by IRMA or by HPLC for ustekinumab produced in CHO cells and monosialylated glycan species were at very low levels based on HPLC analysis and undetectable by IRMA analysis (see, e.g., Table 5 and FIG. 8).

TABLE 5

Representative results for IRMA and HPLC analysis of total neutral, total charged, and other selected oligosaccharide species for ustekinumab produced in Sp2/0 cells and CHO cells

| | IRMA | | HPLC | |
|---|---|---|---|---|
| Glycans | Sp2/0 | CHO | Sp2/0 | CHO |
| G0F | 26.7 | 71.0 | 25.0 | 78.0 |
| G1F | 29.2 | 13.3 | 33.2 | 15.2 |
| G2F | 8.6 | 1.5 | 7.8 | 2.2 |
| Other neutral | 11.0 | 14.2 | 5.9 | 4.2 |
| Total neutral | 75.5 | 100.0 | 71.9 | 99.6 |
| Monosialylated | 20.9 | 0.0 | 25.9 | 0.4 |
| Disialylated | 3.5 | 0.0 | 2.2 | <LOD |
| Total charged | 24.5 | 0.0 | 28.1 | 0.4 |

<LOD—below limit of detection
Numbers are % of totals

TABLE 6

Representative results for IRMA analysis of individual oligosaccharide species for ustekinumab produced in Sp2/0 cells and CHO cells

| Glycan | Sp2/0 Cells % of Total Assigned | CHO Cells % of Total Assigned |
|---|---|---|
| G0F | 26.7 | 71.0 |
| G1F | 29.2 | 13.3 |
| G2F | 8.6 | 1.5 |
| G0 | 2.9 | 10.1 |
| G1FS | 9.7 | 0.0 |
| H6N4F1 | 1.6 | 0.0 |
| G2FS | 7.4 | 0.0 |
| H7N4F1 | 0.9 | 0.0 |
| H6N4F1S1 | 3.9 | 0.0 |
| G2FS2 | 3.5 | 0.0 |
| *Man5 + Lys | 0.7 | 0.9 |
| *G1F-GlcNAc + Lys | 1.1 | 0.6 |
| *H5N3 + Lys | 0.8 | 0.8 |
| *G1 + Lys | 1.5 | 1.2 |
| *G2 + Lys | 0.4 | 0.2 |
| **G1F-GlcNAc − Lys | 0.0 | 0.0 |
| **H5N3 − Lys | 0.0 | 0.0 |
| **G1 − Lys | 0.0 | 0.0 |
| **H5N4 − Lys | 0.0 | 0.5 |
| **H5N3F1 + Lys | 1.0 | 0.0 |

Conclusion

Thus, as described supra, manufacturing control strategies are developed to maintain consistent drug substance (DS) and drug product (DP) characteristics of therapeutic proteins with regard to oligosaccharide profile and/or other characteristics of the DS or DP (e.g., DS and/or DP comprising the therapeutic antibody ustekinumab). In particular, controlling the oligosaccharide profile of therapeutic antibodies is critical because changes in the oligosaccharide profile can significantly affect antibody biological functions. A point of control for the oligosaccharide profile of therapeutic antibodies is the selection of the cellular host for expression of the therapeutic antibodies. As presented herein, ustekinumab expressed in Sp2/0 cells comprises anti-IL-12/IL-23p40 antibodies having a heavy chain (HC) comprising amino acid sequence of SEQ ID NO: 10 and a light chain (LC) comprising amino acid sequence of SEQ ID NO:11; a heavy chain variable domain amino acid sequence of SEQ ID NO:7 and a light chain variable domain amino acid sequence of SEQ ID NO:8; the heavy chain CDR amino acid sequences of SEQ ID NO:1, SEQ ID NO:2, and SEQ ID NO:3; and the light chain CDR amino acid sequences of SEQ ID NO:4, SEQ ID NO:5, and SEQ ID NO:6; wherein the oligosaccharide profile of the anti-IL-12/IL-23p40 antibodies comprises total neutral oligosaccharide species≥64.8% to ≤85.4%, total charged oligosaccharide species≥14.4% to ≤35.6%, and individual neutral oligosaccharide species G0F≥11.5% to ≤40.2%, G1F≥29.9% to ≤40.6%, and G2F≥4.1% to ≤11.3%. Furthermore, the peak 3 area % of the capillary isoelectric focusing (cIEF) electropherogram of the anti-IL-12/IL-23p40 antibodies produced in Sp2/0 cells is ≥39.8% to ≤64.4%.

In contrast, for ustekinumab produced in CHO cells, the oligosaccharide profile is shifted toward very low levels of charged glycans and higher levels of neutral glycans that are predominantly G0F. The oligosaccharide profile for ustekinumab produced in CHO cells comprises anti-IL-12/IL-23p40 antibodies having a heavy chain (HC) comprising amino acid sequence of SEQ ID NO: 10 and a light chain (LC) comprising amino acid sequence of SEQ ID NO:11; a heavy chain variable domain amino acid sequence of SEQ ID NO:7 and a light chain variable domain amino acid sequence of SEQ ID NO:8; the heavy chain CDR amino acid sequences of SEQ ID NO:1, SEQ ID NO:2, and SEQ ID NO:3, and the light chain CDR amino acid sequences of SEQ ID NO:4, SEQ ID NO:5, and SEQ ID NO:6; wherein the oligosaccharide profile of the anti-IL-12/IL-23p40 antibodies comprises total neutral oligosaccharide species>99.0%, total charged oligosaccharide species<1.0%, and individual neutral oligosaccharide species G0F>70.0%, G1F<20.0%, and G2F<5.0%. The peak 3 area % of the capillary isoelectric focusing (cIEF) electropherogram of ustekinumab produced in CHO cells is >70.0%. Furthermore, no disialylated glycan species were detected by IRMA or by HPLC for ustekinumab produced in CHO cells and monosialylated glycan species were at very low levels based on HPLC analysis and undetectable by IRMA analysis. The reduction in sialylated species generally and the reduction of Neu5Gc specifically for ustekinumab produced in CHO cells may provide a benefit by reducing undesirable immunogenic responses when administered to humans. For example, reduced levels of Neu5Gc could reduce clearance so that anti-IL-12/23p40 antibodies produced in CHO cells would have a longer half-life compared to anti-IL-12/23p40 antibodies expressed in Sp2/0 cells, especially for patient populations with higher levels of anti-Neu5Gc antibodies.

What is claimed:

1. A method of manufacture for producing an anti-IL-12/IL-23p40 antibody comprising amino acid sequences selected from the group consisting of: (i) a heavy chain (HC) comprising the amino acid sequence of SEQ ID NO:10 and a light chain (LC) comprising the amino acid sequence of SEQ ID NO:11; (ii) a heavy chain variable domain amino acid sequence of SEQ ID NO:7 and a light chain variable domain amino acid sequence of SEQ ID NO:8; and (iii) heavy chain CDR amino acid sequences of SEQ ID NO:1, SEQ ID NO:2, and SEQ ID NO:3, and light chain CDR amino acid sequences of SEQ ID NO:4, SEQ ID NO:5, and SEQ ID NO:6, wherein the anti-IL-12/IL-23p40 antibody is produced by the steps of:

a. culturing a Chinese Hamster Ovary cell (CHO cell) with nucleotides encoding the anti-IL-12/IL-23p40 antibody;

b. expressing the anti-IL-12/IL-23p40 antibody in the CHO cell;

c. purifying the anti-IL-12/IL-23p40 antibody; and d. determining that the oligosaccharide profile of the anti-IL-12/IL-23p40 antibody comprises total neutral oligosaccharide species>99.0%, total charged oligosaccharide species<1.0%, and individual neutral oligosaccharide species G0F>70.0%, G1F<20.0%, and G2F<5.0%.

2. The method of manufacture of claim 1, wherein the method further comprises determining that the peak 3 area % of the capillary isoelectric focusing (cIEF) electropherogram of the anti-IL-12/IL-23p40 antibody is >70.0%.

3. The method of manufacture of claim 1, wherein the anti-IL-12/IL-23p40 antibody has no disialylated glycan species as determined by High Performance Liquid Chromatography (HPLC) or Reduced Mass Analysis (RMA).

4. The method of manufacture of claim 1, wherein the anti-IL-12/IL-23p40 antibody has a longer half-life compared to an anti-IL-12/IL-23p40 antibody with identical amino acid heavy chain and light chain sequences expressed in Sp2/0 cells.

* * * * *